United States Patent
Kouchi et al.

(10) Patent No.: US 8,781,751 B2
(45) Date of Patent: Jul. 15, 2014

(54) BIOLOGICAL INFORMATION TREND DISPLAY DEVICE AND METHOD THEREOF

(75) Inventors: Kenji Kouchi, Osaka (JP); Ryuji Nagai, Osaka (JP); Shinya Nagata, Osaka (JP)

(73) Assignee: Nihon Kohden Corporation, Tokyo (JP)

( * ) Notice: Subject to any disclaimer, the term of this patent is extended or adjusted under 35 U.S.C. 154(b) by 17 days.

(21) Appl. No.: 12/791,591

(22) Filed: Jun. 1, 2010

(65) Prior Publication Data

US 2010/0238192 A1    Sep. 23, 2010

Related U.S. Application Data

(62) Division of application No. 10/525,749, filed as application No. PCT/JP03/10735 on Aug. 26, 2003, now abandoned.

(30) Foreign Application Priority Data

Aug. 27, 2002    (JP) ................. 2002-246633

(51) Int. Cl.
| | |
|---|---|
| *G06F 19/00* | (2011.01) |
| *A61B 5/00* | (2006.01) |
| *G01D 1/18* | (2006.01) |
| *A61B 5/044* | (2006.01) |
| *G01D 7/02* | (2006.01) |
| *G01D 7/00* | (2006.01) |

(52) U.S. Cl.
CPC ............. *G06F 19/3406* (2013.01); *A61B 5/044* (2013.01); *G01D 1/18* (2013.01); *G01D 7/02* (2013.01); *G01D 7/005* (2013.01)
USPC ............................................. 702/19; 600/301

(58) Field of Classification Search
CPC ...... G06F 19/34; G06F 19/3406; A61B 5/742; A61B 5/02455; A61B 5/044; A61B 5/72
USPC .................... 715/700, 764, 771, 772, 774
See application file for complete search history.

(56) References Cited

U.S. PATENT DOCUMENTS

| | | | |
|---|---|---|---|
| 4,340,065 | A | 7/1982 | Gessman |
| 4,625,278 | A | 11/1986 | Wong |

(Continued)

FOREIGN PATENT DOCUMENTS

| | | |
|---|---|---|
| EP | 0569670 | 11/1993 |
| EP | 1178288 | 2/2002 |

(Continued)

OTHER PUBLICATIONS

Marieb, E. N. Human Anatomy & Physiology. (Benjamin Cummings, 2001). Excerpt of p. 700.*

(Continued)

*Primary Examiner* — Soren Harward
(74) *Attorney, Agent, or Firm* — Jason H. Vick; Sheridan Ross, PC

(57) ABSTRACT

A biological information trend display device and method which allow the trend and an abnormal value of biological information to be checked with ease are provided. When a curve (50) showing the ST level in lead V3 exceeds the upper limit of a normal range, the part of the curve above the upper limit is displayed in an abnormal color "b" (red, for example). To indicate that the ST level derived from the lead V3 has exceeded the upper limit, a lead icon (32) in an upper part of the display screen is displayed in the abnormal color "b."

22 Claims, 10 Drawing Sheets

(56) References Cited

U.S. PATENT DOCUMENTS

| | | | |
|---|---|---|---|
| 4,809,705 A | | 3/1989 | Ascher |
| 5,199,439 A | | 4/1993 | Zimmerman et al. |
| 5,224,486 A | * | 7/1993 | Lerman et al. ............... 600/509 |
| 5,233,515 A | * | 8/1993 | Cosman ........................ 600/549 |
| 5,262,944 A | * | 11/1993 | Weisner et al. ............... 600/300 |
| 5,319,363 A | | 6/1994 | Welch et al. |
| 5,438,983 A | | 8/1995 | Falcone |
| 5,631,825 A | | 5/1997 | van Weele et al. |
| 5,772,599 A | * | 6/1998 | Nevo et al. ................... 600/483 |
| 5,807,246 A | | 9/1998 | Sakaguchi et al. |
| 5,819,741 A | | 10/1998 | Karlsson et al. |
| 5,860,918 A | | 1/1999 | Schradi |
| 5,941,820 A | * | 8/1999 | Zimmerman ................. 600/300 |
| 6,017,307 A | * | 1/2000 | Raines ......................... 600/300 |
| 6,188,407 B1 | * | 2/2001 | Smith et al. .................. 715/841 |
| 6,370,423 B1 | * | 4/2002 | Guerrero et al. ............. 600/513 |
| 6,806,891 B1 | | 10/2004 | Manuel et al. |
| 2002/0068962 A1 | * | 6/2002 | Ferek-Petric ................. 607/60 |
| 2002/0156352 A1 | * | 10/2002 | Eggers ......................... 600/300 |
| 2003/0013978 A1 | * | 1/2003 | Schlegel et al. ............. 600/509 |
| 2003/0018241 A1 | * | 1/2003 | Mannheimer ................. 600/300 |
| 2005/0246366 A1 | | 11/2005 | Kouchi et al. |

FOREIGN PATENT DOCUMENTS

| | | | |
|---|---|---|---|
| JP | 51-787 | 1/1976 | |
| JP | 63-201524 | 8/1988 | |
| JP | 04-290917 | 10/1992 | |
| JP | 04-306696 | 10/1992 | |
| JP | 04-352939 | 12/1992 | |
| JP | 05-154117 | 6/1993 | |
| JP | 06-142071 | 5/1994 | |
| JP | 06-181898 | 7/1994 | |
| JP | 06-261871 | 9/1994 | |
| JP | 08-129579 | 5/1996 | |
| JP | 09-229721 | 9/1997 | |
| JP | 10-198658 | 7/1998 | |
| JP | 2001-293761 | 10/2001 | |
| WO | WO 82/00949 | * 4/1982 | ............... A61B 5/02 |

OTHER PUBLICATIONS

Zanden, B. Vander & Myers, B. A. Automatic, look-and-feel independent dialog creation for graphical user interfaces. in Proc. SIGCHI Conf. Hum. Factors Comput. Syst. 27-34 (ACM Press, 1990).*

Newlan et al., "Implementing a continuous 12 lead ST Monitoring system," 18th Annual International Conference of the IEEE Engineering in Medicine and Biology Society, Amsterdam, 5.4.1, ECG, ST-segment and Ischemia, 1996, pp. 1355-1356.

Supplementary European Search Report for European Application No. 03795234.8, dated Mar. 23, 2009.

International Preliminary Report on Patentability for International (PCT) Application No. PCT/JP2003/010735, completed Jun. 30, 2004.

Official Action for European Application No. 03795234.8, dated Jul. 8, 2009.

Official Action for U.S. Appl. No. 10/525,749, mailed Sep. 28, 2007.

Official Action for U.S. Appl. No. 10/525,749, mailed Mar. 27, 2008.

Official Action for U.S. Appl. No. 10/525,749, mailed Dec. 26, 2008.

Final Official Action for U.S. Appl. No. 10/525,749, mailed Jul. 24, 2009.

Official Action for U.S. Appl. No. 10/525,749, mailed Jul. 7, 2010.

Decision on Appeal for U.S. Appl. No. 10/525,749, mailed Jun. 22, 2012.

Examiner's Summary of Interview for U.S. Appl. No. 10/525,749, mailed Jul. 30, 2012.

Official Action for U.S. Appl. No. 10/525,749, mailed Nov. 26, 2012.

* cited by examiner

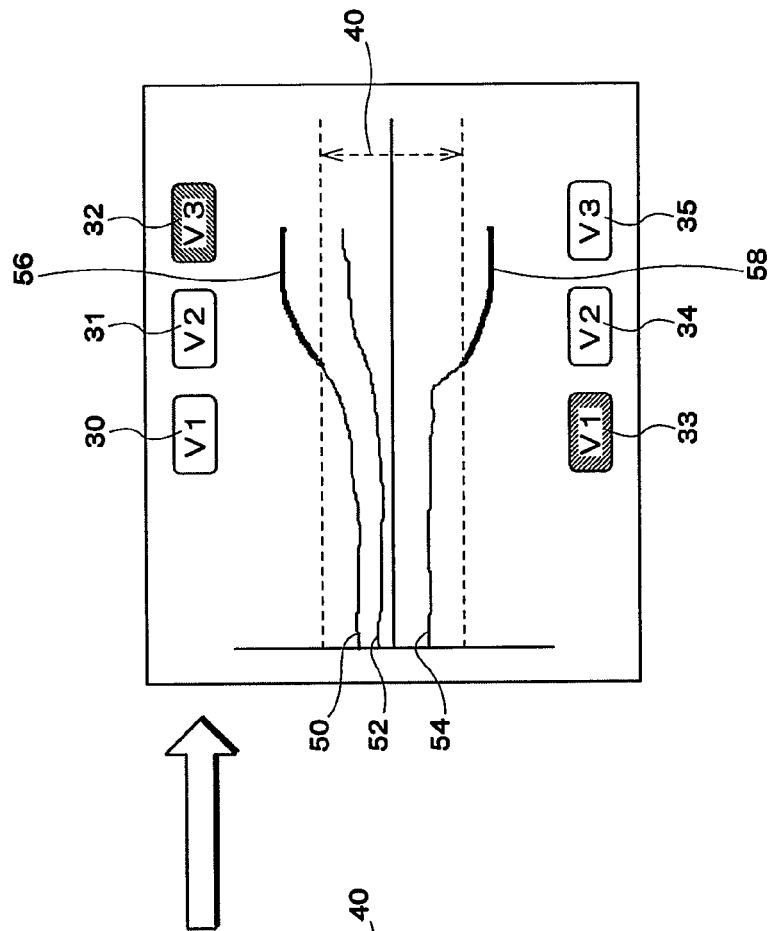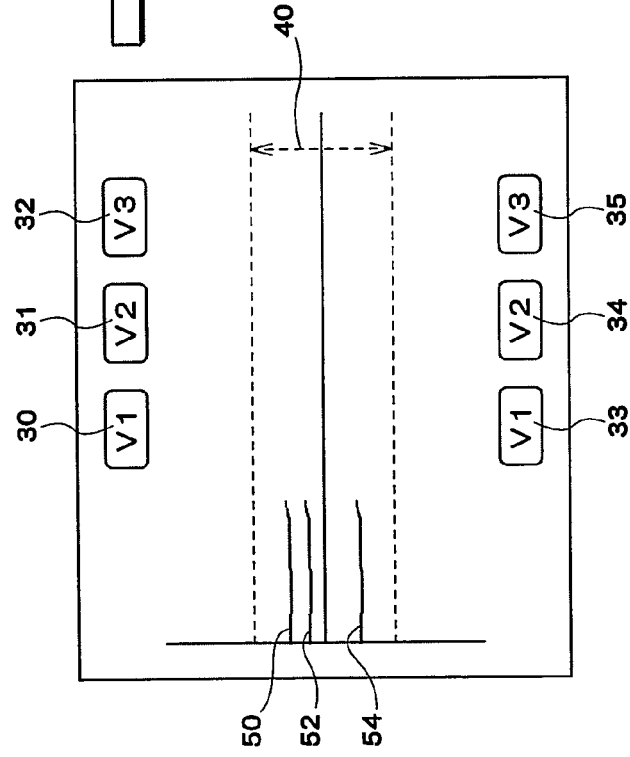

FIG.9A

| No. | ST (mv) | RR (sec) | ... |
|---|---|---|---|
| -4 | 0.05 | 0.68 | ... |
| -3 | -0.01 | 0.80 | ... |
| -2 | 0.03 | 0.72 | ... |
| -1 | 0.08 | 0.62 | ... |
| Pre | 0.09 | 0.64 | ... |

FIG.9B

| No. | ST (mv) | RR (sec) | ... |
|---|---|---|---|
| -4 | 0.05 | 0.68 | ... |
| -3 | -0.01 | 0.80 | ... |
| -2 | 0.03 | 0.72 | ... |
| -1 | 1.24 | 0.62 | ... |
| Pre | 0.09 | 0.64 | ... |

BIOLOGICAL INFORMATION TREND DISPLAY DEVICE AND METHOD THEREOF

CROSS-REFERENCE TO RELATED APPLICATIONS

The present application is a divisional of U.S. application Ser. No. 10/525,749 filed Feb. 25, 2005, which is a national stage application under 35 U.S.C. 371 of PCT Application No. PCT/JP2003/010735 filed Aug. 26, 2003, claims the benefit of patent application number 2002-246633, filed in Japan on Aug. 27, 2002, each of which are hereby incorporated herein by reference.

BACKGROUND OF THE INVENTION

1. Field of the Invention

The present invention relates to a device and a method for displaying a biological information trend and more particularly for facilitating check of the biological information trend.

2. Description of the Related Art

In the technical field of displaying biological information such as blood pressure or electrocardiogram, some techniques have been developed to allow the biological information to be easily checked. There is a technique for displaying an event mark at a time position corresponding to electrocardiographic data during an attack on a trend graph of an electrocardiographic parameter such as heart rate or ST level of electrocardiogram (herein after referred to as "ST level") (see Patent Document 1, for example). Patent Document 1: JP-A-Hei 4-352939 (FIG. 8).

According to the technique, it is possible to determine when attacks occurred with the event marks. That is, according to the existing technique, it is possible to obtain information about when abnormal values of biological information appeared.

In a medical site, however, a technique to allow for easily and simultaneously understanding of trend (or tendency) of a plurality of biological information and their abnormal values in addition to the determination of individual abnormal values may be demanded.

SUMMARY OF THE INVENTION

In one aspect, the invention provides a biological information trend display device and method thereof that are capable of facilitating check of the biological information trend and identification of abnormal value. The invention includes the following:

(1) A biological information trend display device in accordance with the present invention for displaying a time-series trend of biological information, comprises means for obtaining a plurality of biological information, means for determining whether the obtained biological information is abnormal biological information or not, and means for displaying time-series trend for each of a plurality of biological information, wherein the displaying means changes trend display style for biological information that is determined as the abnormal biological information.

The user who utilizes the results outputted by the displaying means can easily understand trend of the biological information. For example, if multiple trends of a plurality of biological information are displayed, the user can easily understand that the presence or absence of abnormal biological information and the trend since the determined abnormal biological information is changed its trend display style.

(3) A biological information trend display device in accordance with the present invention for displaying a time-series trend of biological information, comprises means for obtaining a plurality of biological information and information regarding whether the biological information is abnormal biological information or not, and means for displaying time-series trend for each of a plurality of biological information, wherein the displaying means changes trend display style for biological information that is determined as the abnormal biological information.

The user who utilizes the results outputted by the displaying means can easily understand the trend of the biological information. If multiple trends of a plurality of biological information are displayed, the user can easily understand that the presence or absence of abnormal biological information and the trend since the determined abnormal biological information is changed its trend display style.

(4) The device in accordance with the present invention is characterized in that the displaying means further displays biological information determined as the abnormal biological information in association with information relating to the source of the biological information.

The user who utilizes the results outputted by the displaying means can easily understand the trend of determined abnormal biological information and the source for obtaining the biological information (i.e. basis for the determination).

(5) The device in accordance with the present invention is characterized in that the displaying means further displays a source for obtaining biological information that is determined as the abnormal biological information, while not displaying a source for obtaining biological information that is not determined as the abnormal biological information.

The biological information trend display device displays information with respect to the source only for the biological information that is determined as the abnormal biological information. Therefore, the biological information trend display device can effectively execute the announce (or caution, presentation) of information with respect to the trend of determined abnormal biological information and the source for obtaining the biological information in directing the user's greater attention to the information.

(6) The device in accordance with the present invention is characterized in that the determination of the abnormal biological information comprises determination whether the biological information exceeds certain level or falls below certain level, and the displaying means further displays a source for obtaining biological information at an upper portion of the time-series trend when the biological information exceeds certain level, and displays a source for obtaining biological information at a lower portion of the time-series trend when the biological information falls below certain level.

The user who utilizes the results outputted by the displaying means can visually and easily understand the trend of determined abnormal biological information and whether the biological information exceeds the certain level or falls below the certain level.

(7) The device in accordance with the present invention is characterized in that when subsequent biological information of the determined abnormal biological information is not determined as the abnormal biological information, wherein the displaying means further displays the trend of the subsequent biological information in the original style, and maintains the indication of the information relating to the source of the biological information.

Even though the subsequent biological information is not determined as abnormal biological information, the user who utilizes the results outputted by the displaying means can grasp information with respect to a source for obtaining the biological information with a history of abnormal biological information.

(8) The device in accordance with the present invention is characterized in that the displaying means further displays the information relating to the source for obtaining biological information and the source related information allows to discriminate the cases: a case in which current biological information is determined as the abnormal biological information, a case in which past and current biological information are determined as the abnormal biological information, and a case in which past biological information is determined as the abnormal biological information while current biological information is not determined as the abnormal biological information.

Even though the current biological information is not determined as abnormal biological information, the user who utilizes the results outputted by the displaying means can grasp information with respect to a source for obtaining the biological information with a history of abnormal biological information.

(9) The device in accordance with the present invention is characterized in that the device further comprises display area for displaying the information relating to the source of biological information, wherein the display area includes an inner indication area and an outer indication area that surrounds the inner indication area, and wherein the displaying means further displays at least the inner indication area in association with biological information that is determined as the abnormal biological information when current biological information is determined as the abnormal biological information, and displays at least the outer indication area in association with the biological information determined as the abnormal biological information when the biological information is determined as abnormal biological information in the past.

Even though the current biological information is not determined as abnormal biological information, the user who utilizes the results outputted by the displaying means can grasp information with respect to a source for obtaining the biological information with a history of abnormal biological information based on the outer display area.

(10) The device in accordance with the present invention is characterized in that the displaying means further displays time-series trend of biological information with information relating to the source of the biological information.

The user who utilizes the results outputted by the displaying means can visually and easily grasp the multiple trends of a plurality of biological information and sources for obtaining the biological information.

(11) The device in accordance with the present invention is characterized in that the displaying means displays different biological information in the same trend display style, which are derived from different sources for the biological information that is not determined as the abnormal biological information.

The user who utilizes the results outputted by the displaying means can visually and easily understand that the biological information is not determined as the abnormal biological information (i.e. the biological information is normal), even though the user visually check multiple trends of a plurality of biological information at the same time.

(12) The device in accordance with the present invention is characterized in that the changing trend display style comprises changing the trend display color.

For example, if multiple trends of a plurality of biological information are displayed, the user who utilizes the results outputted by the displaying means can visually and easily understand that the presence or absence of abnormal biological information and the trend since the trend display color of biological information is changed to the color for abnormal.

(13) The device in accordance with the present invention is characterized in that the displaying means further conforms the trend display color of biological information that is determined as the abnormal biological information to display color of information relating to the source of the biological information.

The user who utilizes the results outputted by the displaying means can visually and easily understand the trend of determined abnormal biological information and the source for obtaining the biological information.

(14) The device in accordance with the present invention is characterized in that the biological information comprises information that shows different behaviors depending on the sources.

The user who utilizes the results outputted by the displaying means can easily understand the trend of information that changes its behavior according to a source for obtaining the information.

(15) The device in accordance with the present invention is characterized in that the biological information comprises information related to ST level of an electrocardiogram, and the source-related information comprises information relating to electrocardiogram lead.

The user who utilizes the results outputted by the displaying means can understand trend of the information related to ST level and the electrocardiogram lead (hereinafter referred to as the "lead") for obtaining the information.

(16) A biological information trend displayed object in accordance with the present invention, representing time-series trend of the biological information, is characterized in that the biological information trend displayed object represents time-series trend for each of a plurality of biological information, and trend display style for the determined abnormal biological information is changed.

The user who utilizes the biological information trend displayed object can easily understand the trend of the biological information. For example, if multiple trends of the plurality of biological information are displayed, the user can easily understand that the presence or absence of abnormal biological information and the trend since the trend display style of biological information is changed to the style for abnormal.

(17) A data display device in accordance with the present invention is characterized in that for obtaining different types of data in time-series as indicator and displaying each of the obtained data in a graph form, wherein the data display device sets display area for indicating data type, and is to execute the procedures of determining whether content represented based on the obtained data is matter to be informed or not, displaying the data determined as the matter to be informed in a graph form by using different graph display style from that of data not determined as the matter to be informed, and conforming all or a part of display style for indicating the data type to all or a part of the graph display style of the data.

The user can understand both the graph for data determined as the matter to be informed and the data type corresponding to the data in associating with each other.

The followings are definitions of the terms.

In this invention,

"Biological information" is a concept that includes any information which can be obtained from a living body (biological signals, vital signs, etc.). The "biological information" includes individual values (parameters) that represent information about a living body and information which can be obtained based on a plurality of such parameters. In the embodiment, ST levels correspond to this concept.

"Time-series trend" is a concept that includes something which represents information about changes over time in a subject matter (action, variation, behavior, etc. thereof). For example, the concept includes information about changes over time in the difference between a subject matter and a prescribed reference value in addition to changes over time in the subject matter itself. In the embodiment, a trend graph of ST levels corresponds to the concept of "time-series trend."

"Trend display style" is a concept that includes the style of displaying information about changes over time in a subject matter. For example, the concept includes the shapes, types patterns, codes, symbols or colors for the graph showing the changes over time in a subject matter, and the shapes, patterns, codes, symbols or colors of curves (or plot points or indication points) for modifying the graph curves (or plot points or indication points). In the embodiment, the colors or hues of the curves of the ST level trend graph correspond to this concept.

"Abnormal biological information" is a concept that includes biological information which is out of a prescribed normal range (or which does not show a prescribed normal value) or which is within a prescribed abnormal range (or show a prescribed abnormal value). For example, the concept includes biological information which is out of the range within which it falls when a living body is in good (normal, right or ordinary) condition and biological information determined as abnormal (or pathological) by a specific determination method. In the embodiment, an ST level out of the range from −0.1 mV to 0.1 mV corresponds to this concept.

"To determine whether the information is abnormal biological information" includes to determine the presence or absence of abnormal biological information (or the degree of the abnormality thereof), to determine the presence or absence of normal biological information (or the degree of the normality thereof), or to determine whether the information is normal biological information or abnormal biological information, (or to determine the degree of the state).

"Information relating to the source of the biological information" is a concept that includes something representing information used to obtain the biological information. For example, the concept includes the name of the part (source) from which the biological information is obtained, the name of the derivation of the biological information, or the name of the criterion for determining the biological information. In the embodiment, the "name of lead" in which a recognized waveform which can be used to obtain an ST level appears corresponds to this concept.

"Matter to be informed" is a concept that includes anything to be informed. For example, the concept includes something indicating a failure of the device, something useful (or effective) to determine biological information, or something relating to an abnormality of biological information. In the embodiment, information about an ST level in the case where the ST level in an abnormal range corresponds to this concept.

The features of the present invention can be described broadly as set forth above. The structures and characteristics of the present invention will be apparent from the following detailed description of the invention together with those features, effects, and drawings.

BRIEF DESCRIPTION OF THE DRAWINGS

FIGS. 1A and 1B are schematic views illustrating examples of a displayed ST level trend according to an embodiment.

FIGS. 9A and 9B are schematic views of identified value data as an object of the ST level trend creation process.

DESCRIPTION OF THE PREFERRED EMBODIMENTS

Figure 2:
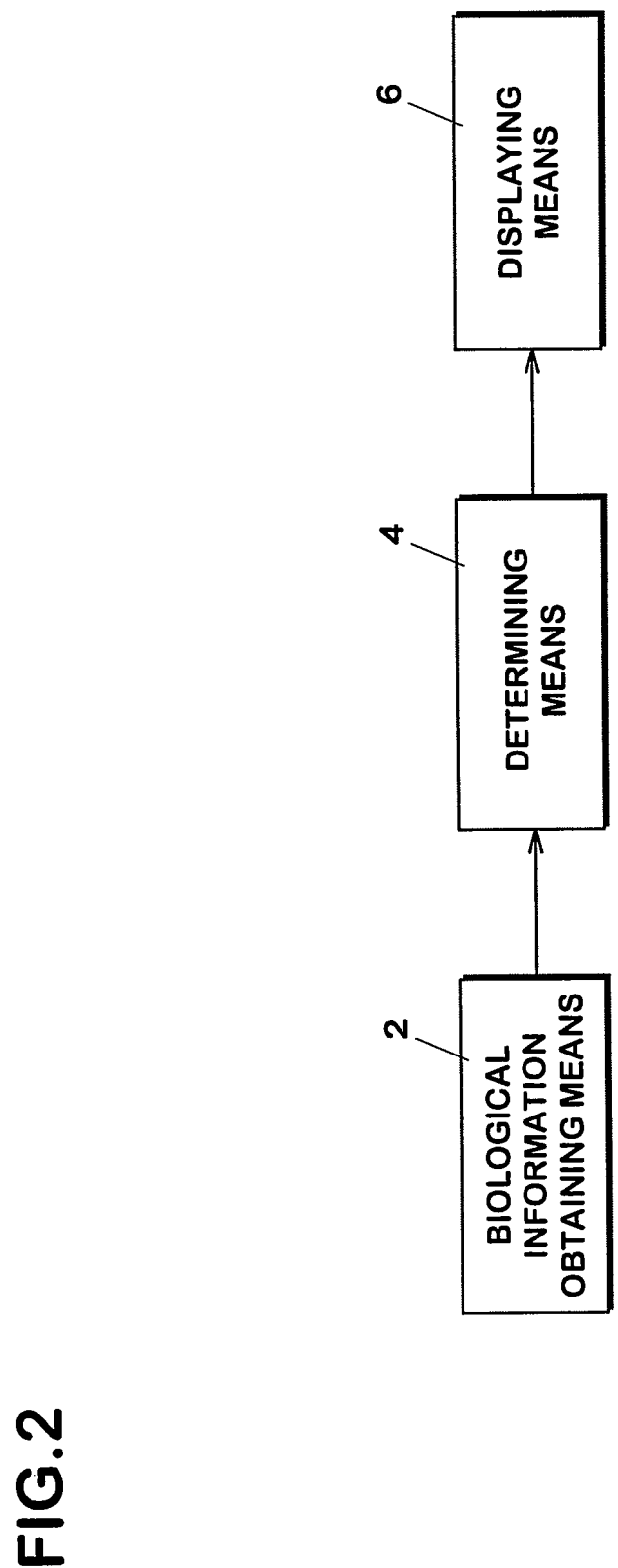
FIG. 2 is a functional block diagram of an ST level trend display device.

An ST level trend display device as an embodiment of the "biological information trend display device" will be described below. The embodiments illustrates process for displaying ST level of the patient ECG data as a trend graph. According to the following embodiments, for example, the device displays ST level trend graphs from all lead waves of 12-lead ECG. In addition, when there is abnormal ST level derived from certain lead(s), the user of the device can intuitively and easily obtain information about from which leads the abnormal ST levels. The 12-lead ECG are twelve-pattern electrocardiograms which are obtained from plurality of to dozen electrodes attached to a living body.

An overview of the embodiments, hardware configurations of devices, embodiments and structures corresponding to the terms in claims, and details of embodiments will be described below.

Table of Contents for the Embodiments
1. Outline of ST Level Trend to be Displayed
2. Hardware configurations of devices
3. Embodiments
4. Example of ST Level Trend to be Displayed
5. ST Level Trend Creation Process etc.
6. Effects of Embodiment
7. Other functions of the ST level trend display device
8. Other embodiments
1. Outline of ST Level Trend to be Displayed An ST level trend is a displayed trend graph of ST levels obtained from electrocardiograms (ECG) of a patient. An ST level trend display device 100 for performing the display will be described later. This device is suitable for the use in emergency situations or in ambulances and hospitals. In this embodiment, description will be made taking as an example a case where it is used by an emergency medical technician in an ambulance carrying a patient.

FIG. 1 is a schematic view illustrating an example of a displayed ST level trend graph. In the drawing, for example, the trends of ST levels recognized from lead waveforms derived from leads V1, V2 and V3 are displayed simultaneously (in parallel) in the graph. The vertical axis and horizontal axis of the ST level trend graph represent voltage (mV) and time (minute), respectively. The ST level trend graph is drawn (plotted) from left to right on the display screen as the measurement of electrocardiograms proceeds.

The items shown in FIG. 1 are as follows.

A lead icon 30 representing the lead V1, a lead icon 31 representing a lead V2 and a lead icon 32 representing the lead V3 are displayed in an upper part of the display screen. A lead icon 33 representing the lead V1, a lead icon 34 representing the lead V2 and a lead icon 35 representing the lead V3 are displayed in a lower part of the display screen. A curve 50 showing the ST level in the lead V3, a curve 52 showing the ST level in the lead V2, and a curve 54 showing the ST level in the lead V1 are also displayed on the display screen.

FIG. 1A shows the state in which the ST levels recognized from the lead waveforms derived from the leads V1, V2 and V3 are all in the normal range (−0.1 mV to 0.1 mV). The normal range is the range indicated by a dotted line arrow 40 (the dotted line arrow 40, which is shown for explanation and thus is not displayed on a display screen 14, may be displayed). In FIG. 1A, all the curves 50, 52 and 54 are displayed in a normal value color "a" (blue, for example) to indicate that the values are in the normal range. The backgrounds (areas) of all the lead icons 30 to 35 (or the letters representing the names of the leads) are also displayed in the normal value color "a".

FIG. 1B shows the state in which some measurement time has passed from the moment shown in FIG. 1A and some of the ST levels recognized from the lead waveforms are out of the normal range.

In FIG. 1B, a curve segment 56 showing the ST level in the lead V3 is above the upper limit of the normal range, and the part of the curve above the upper limit is displayed in an abnormal value color "b" (red, for example) (change of trend display color). To indicate that the ST level derived from the lead V3 has exceeded the upper limit, the lead icon 32 in the upper part of the display screen (above the time-series trend) is also displayed in the abnormal value color "b" as shown in the drawing (the trend of biological information and the information relating to the source of the biological information are displayed in the same color).

Also in FIG. 1B, a curve segment 58 showing the ST level in the lead V1 is below the lower limit of the normal range, and the part of the curve below the lower limit is displayed in an abnormal value color "c" (yellow, for example). To indicate that the ST level derived from the lead V1 has become lower than the lower limit, the lead icon 33 in the lower part of the display screen (below the time-series trend) is also displayed in the abnormal value color "c" as shown in the drawing.

According to the display as described above, the trends of ST levels recognized from a plurality of lead waveforms can be displayed simultaneously. Also, when one or more of the ST levels show abnormal values, information about leads from which the ST levels are derived can be visually recognized with ease.

Although each graph curve and the corresponding lead icon are displayed in the same color "to display the trend of biological information and the information relating to the source of the biological information in the same color" in the above embodiment, the present invention is not limited thereto. The state in which displayed colors are "the same" includes the case in which two or more colors can be determined to be visually similar (or close) to each other.

In the embodiment, each ST level is the value (mV) at a point (ST1) 60 msec after the inflection point of an ST segment. The measurement point of ST level may be changed by means known to those skilled in the art. For example, STj, ST1, or ST2 may be used.

2. Hardware Configurations of Devices

FIG. 2 illustrates a function block diagram of a ST level trend display device. The ST level trend display device includes biological information obtaining means 2, determining means 4, and displaying means 6.

The biological information obtaining means 2 obtains biological information (or biological signal or vital sign). The determining means 4 determines whether the biological information represents a normal value or an abnormal value (or whether a living body condition represented by the biological information is normal condition or abnormal condition). The displaying means 6 displays a biological information trend in a trend display style that is based on the determination result.

Figure 3:
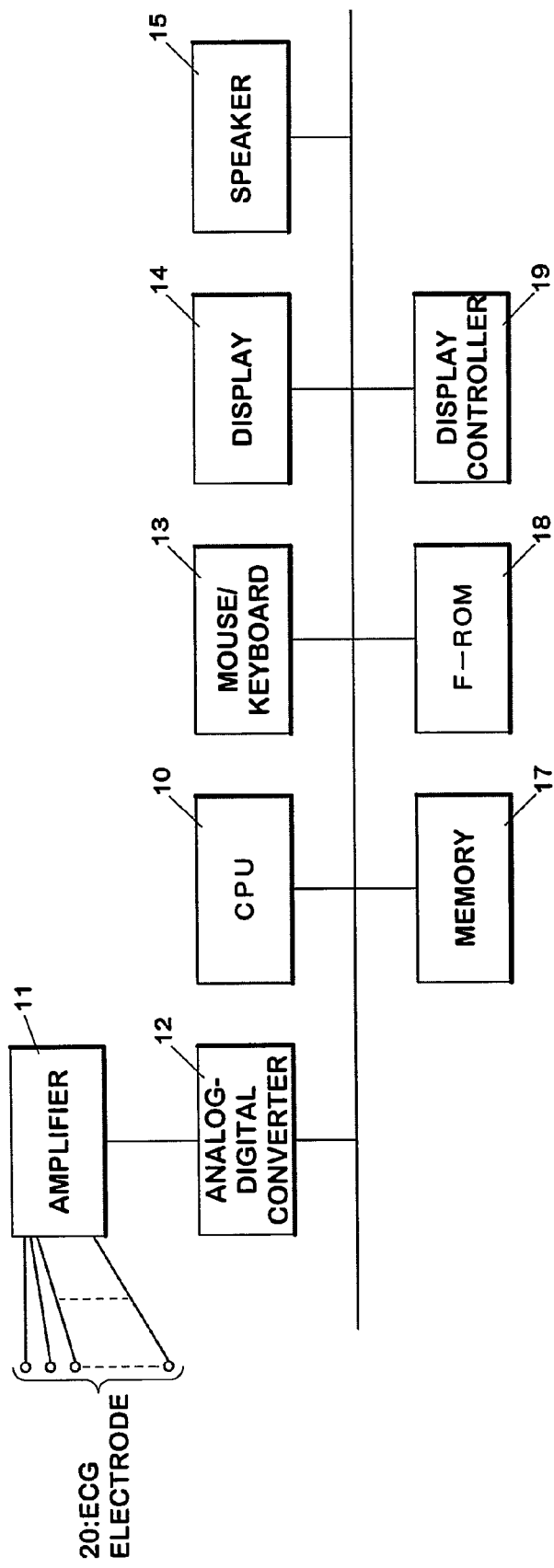
FIG. 3 is an example of the hardware configuration of the ST level trend display device.

FIG. 3 illustrates a hardware configuration example of the ST level trend display device shown in FIG. 2 by use of a central processing unit (CPU). The ST level trend display device 100 includes CPU 10, amplifier 11, analog-digital converter 12, mouse/keyboard 13, display 14 (display device), speaker 15, memory 17, Flash-ROM 18 (which corresponds to a rewritable read-only memory device from which recorded data can be electrically erased (e.g. the flash-memory), and will be described as "F-ROM 18"), display controller 19, and ECG electrodes 20 (biological signal detector).

The ECG electrodes 20 are used for measuring a cardiac electric current. The amplifier 11 amplifies the cardiac electrical current obtained through ECG electrodes 20. The CPU 10 controls operations of the ST level trend display device 100, executes a process that converts data obtained from the cardiac electric current to ECG data (or identified value data), and executes a process that generates a ST level trend. The F-ROM 18 stores a computer program for controlling the ST level trend display device 100. The memory 17 acts as a storage area for data processing performed by the CPU 10. Operation information generated via operations of the mouse/keyboard 13 or the display controller 19 is inputted to the CPU 10, and the CPU 10 generates display information and sound information for the display 14 and the speaker 15 to output.

In the embodiments, examples of operating systems (OS) for the ST level trend display device 100 are MICROSOFT WINDOWS® XP, NT, 2000, 98SE, ME, or CE. In alternative embodiments, the functions of the ST level trend display device 100 are accomplished with hardware logic (not shown) without the use of a CPU. The hardware configuration or CPU configuration can be modified by well-known techniques by those skilled in the art.

The "ECG" described in the embodiments is obtained by measuring cardiac electrical potential difference on the heart between two points on the patient's body. Therefore, the terms "ECG measurement" etc. used herein include the operations of measuring the cardiac electrical potential etc.

3. Embodiments

The "biological information trend display device" includes any device that displays biological information trend. For example, the "biological information trend display device" corresponds to ST level trend display device 100 illustrated in FIG. 3 as an embodiment. The "biological information obtaining means" includes any means that has a function for obtaining biological information. In the embodiments, the biological information obtaining means corresponds to CPU 10 of the ST level trend display device 100 that executes a process of step S605 in FIG. 6 for plurality of lead waveforms. The "determining means" includes any means that has a function for determining whether obtained biological information corresponds to abnormal biological information or not. In the embodiments, the determining means corresponds to CPU 10 that executes a process of step S613 in FIG. 6. The "displaying means" includes any means that has a function of displaying. In the embodiments, the displaying means corresponds to CPU 10 that executes a process of step S615, S623, S619, or step S621.

4. Example of ST Level Trend to be Displayed

Figure 5:
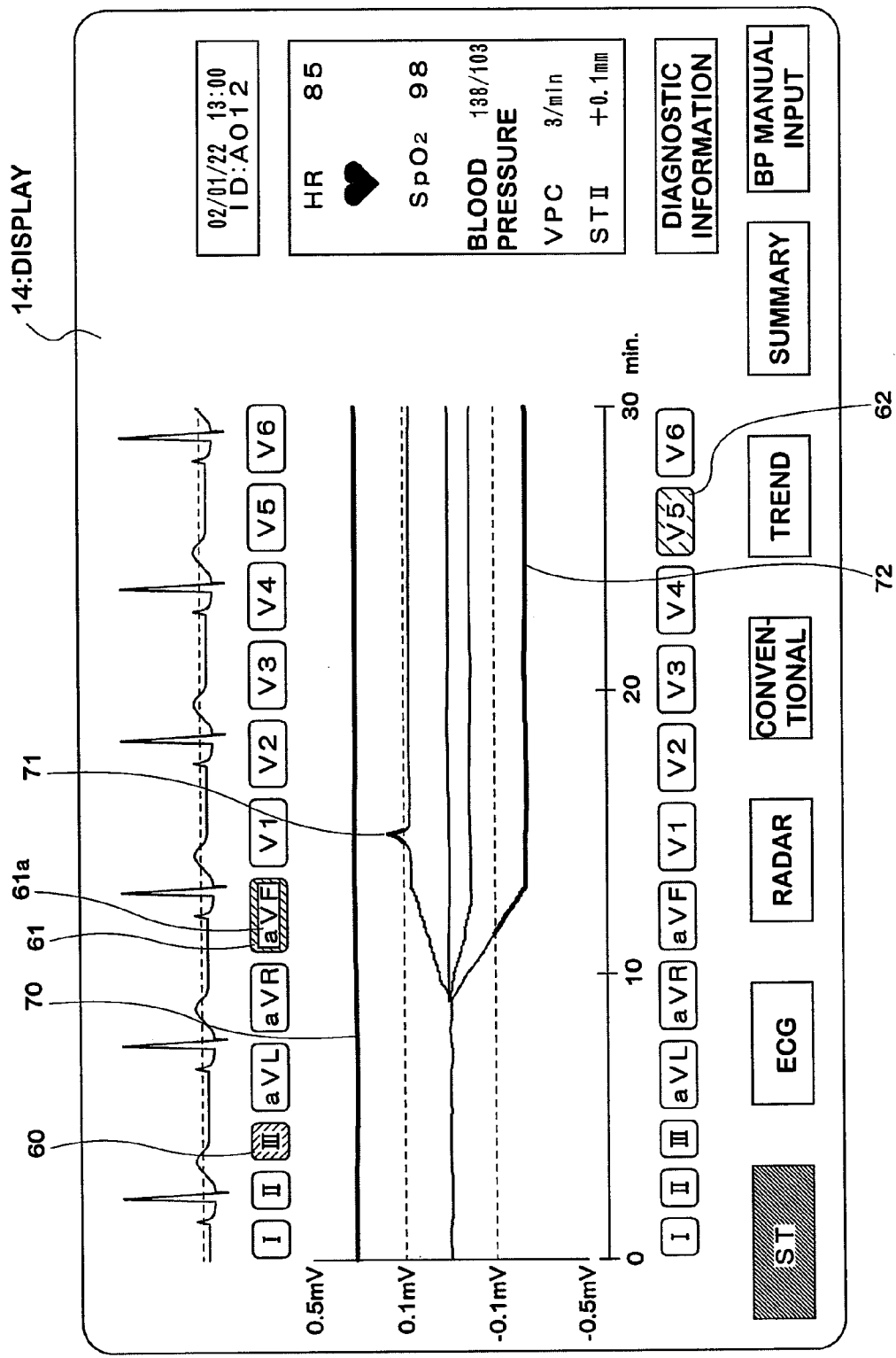
FIG. 5 is an example of a screen displayed on the ST level trend display device.

Description will be made of an example of an ST level trend to be displayed. The ST level trend creation process will be described in the next section. FIG. 5 is an example of the screen displayed by a ST level trend creation process (which will be described later) performed by the CPU 10.

As shown in FIG. 5, ST level trend curves obtained from identified value (recognized value) data of waveforms derived from 12 leads are displayed on the display screen 14.

The 12 leads are leads I, II, III, aVL, aVR, $aV_F$, V1, V2, V3, V4, V5 and V6. Lead icons representing them are displayed in upper and lower parts of the display screen 14. The areas in which the lead icons (types of data) are displayed (data type indication area) are located in fixed positions on the display screen (the indication area of the information relating to the source of biological information is associated with each information relating to the source). Thus, 12 ST level trend curves are displayed on the display screen 14 (curves showing similar values may overlap with each other).

The vertical axis and horizontal axis of the ST level trend graph represent voltage (in the range from −0.5 mV to 0.5 mV) and time (min.), respectively. More specifically, the area from left to right of the display screen 14 is a graph display area corresponding to a measurement period of 30 min. The upper and lower limits of the normal range of the ST levels are 0.1 mV and −0.1 mV, respectively. The upper and lower limits are indicated by dotted lines on the display screen 14. The display of the dotted lines on the display screen may be omitted.

A plot point moves (to the right on the display screen) as the measurement of electrocardiograms proceeds and draws the ST level trend graph. In FIG. 5, the drawing point is currently at a point about 30 minutes after the start of the measurement. The parts of the curves within the normal range are displayed in the normal value color "a" (blue, for example).

In FIG. 5, a case in which some of the ST levels of the waveforms derived from the 12 leads show abnormal values is shown as an example. Each of the abnormal values will be described.

A curve 70 showing the ST level of the lead waveform derived from the lead III is above the upper limit and displayed (plotted) in an abnormal value color X (graph display style). To indicate that the ST level derived from the lead III is higher than the upper limit, a lead icon 60 (for the lead III) in the upper part of the display screen is displayed in the same abnormal value color X as the curve 70 in the drawing (the type of data is displayed in the same style as the curve of the data).

A curve 72 showing the ST level of the waveform derived from the lead V5 has become lower than the lower limit, and the part of the curve below the lower limit is displayed in an abnormal value color Y. To indicate that the ST level derived from the lead V5 has become lower than the lower limit, a lead icon 62 (for the lead V5) in the lower part of the display screen is displayed in the same abnormal value color Y as the curve 72 in the drawing.

A curve 71 showing the ST level of the waveform derived from the lead $aV_F$ has a part above the upper limit and the part is displayed in an abnormal value color Z. To indicate that the ST level derived from the lead $aV_F$ was higher than the upper limit, an outer frame 61 of a lead icon (for the lead $aV_F$) in the upper part of the display screen is displayed in the same abnormal value color Z as the part above the upper limit of the curve 71. An inner area 61*a* of the lead icon is displayed in the normal value color since the ST level derived from the lead $aV_F$ has returned to the normal range.

FIG. 10 is a schematic view illustrating the changes in the display style of a lead icon described above.

Figure 10A:
FIGS. 10A, 10B and 10C are schematic views illustrating the changes in the display style of a lead icon.

FIG. 10A shows an example of a lead icon 500 (for the lead V5) in the case where the ST level has been in the normal range. In this case, the lead icon 500 is displayed in a normal value color P.

Figure 10B:
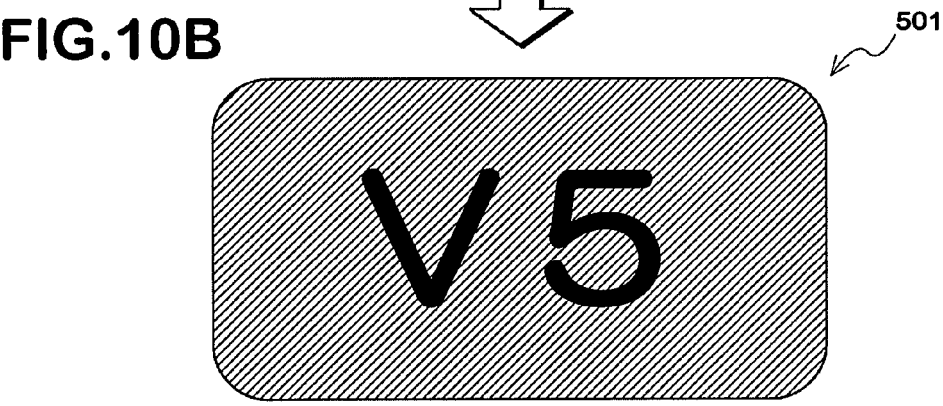

FIG. 10B shows an example of a lead icon 501 in the case where the ST level shows an abnormal value at the present time (or at the moment when the ST level was displayed). In this case, the lead icon 501 is displayed in an abnormal value color Q. At this time, the abnormal value color Q is the same as the color of the trend curve (or the part of the curve in the abnormal range) of the ST level in the corresponding lead V5 (which corresponds to "when the current biological information is determined as abnormal biological information, the display means displays at least the inner indication area in association with the biological information determined as abnormal biological information").

Figure 10C:
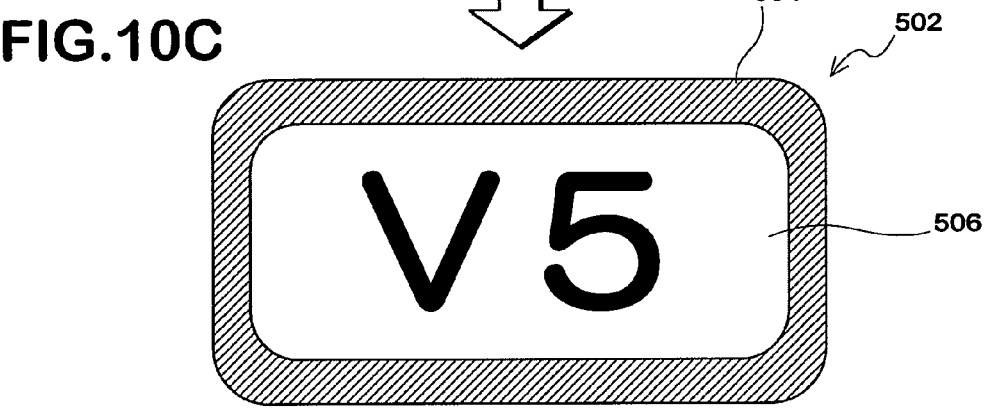

FIG. 10C shows an example of a lead icon 502 in the case where some time has passed from the moment shown in FIG. 10B and the ST level in the lead V5 has returned to the normal range. In this case, an icon frame 504 (outer indication area) of the lead icon 502 is maintained in the abnormal value color Q (which corresponds to "when the biological information is determined as abnormal biological information in the past, the display means displays at least the outer indication area in association with the biological information determined as abnormal information"). At this time, an inner area 506 (inner indication area) of the icon is displayed in the normal value color P.

The shape of the ST level trend graph, the direction in which the graph is created as time passes, the style of displaying the curves, the style of displaying the names of leads, the style of displaying normal and abnormal values (colors, etc.) are illustrative and may be changed by means known to those skilled in the art.

For example, when the ST levels are in the normal range, the ST level curves and the corresponding leads icons may be displayed in different colors.

Unlike the curve 71 and the lead icon 61 shown in FIG. 5, when there was a period in which an ST level was out of the normal range in the history but the ST level has returned to the normal range, the parts of the curve 71 in the normal range may be displayed in the normal value color with the entire lead icon (the outer frame 61 and the inner area 61*a*) displayed in an abnormal value color (which corresponds to "when the subsequent biological information is not determined as abnormal information, the display means displays the trend of the subsequent biological information in the original style and maintains the indication of the information relating to the source of the biological information"). The present invention is not limited to the above example. When the value returns to the normal range, the entire corresponding lead icon may be returned to the normal value color (return the indication of the information relating to the source of the subsequent biological information (cancel the association of it with the biological information)).

Although only the part of the curve above the normal range is displayed in an abnormal value color in FIG. 5, the present invention is not limited thereto. When an ST level gets out of the normal range, the entire curve may be displayed in an abnormal value color (the entire style of displaying is changed for the trend of biological information determined as abnormal biological information).

In the preferred embodiment shown in FIG. 5, the curve 70 and the lead icon 60 are displayed in the same abnormal value color X to associate them with each other and the part of the curve 72 in the abnormal range and the lead icon 62 are displayed in the same abnormal value color Y to associate them with each other. Thus, even when a plurality of ST levels show abnormal values, it is possible to determine the lead (source or base) from which each ST level is derived easily. However, the present invention is not limited to this. When there is no need to associate abnormal values with their sources, the association by changing the colors may be omitted.

The electrocardiogram of the lead II as a representative lead and so on are also displayed on the display screen 14. The electrocardiogram can be displayed in a different style depending on the selection of the user. An electrocardiogram of another lead may be displayed or the display may be omitted. In this embodiment, a lead in which the amplitude is large is automatically selected and displayed as a representative lead.

Figure 4:
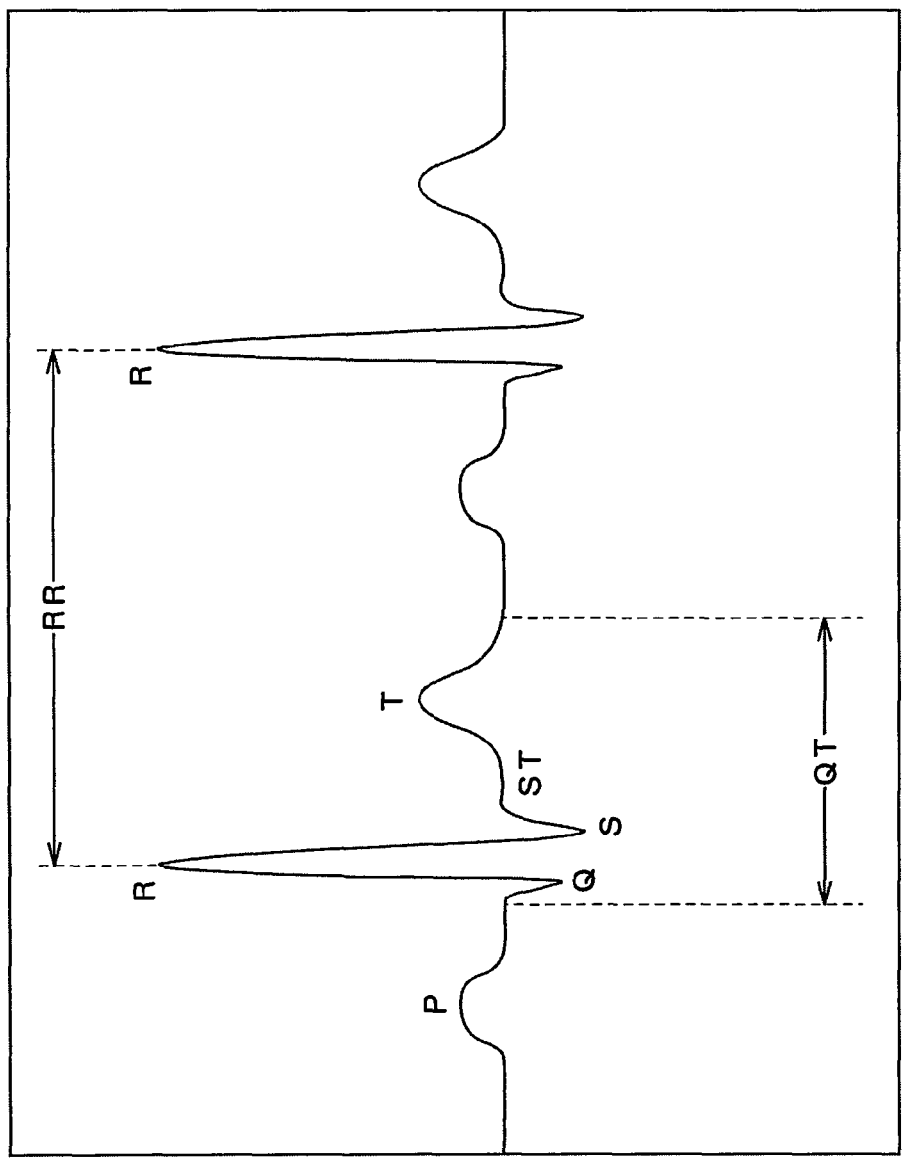
FIG. 4 is a graph schematically illustrating recorded electrocardiographic waveform data.

The CPU 10 continuously records digital data (electrocardiographic waveform data) obtained via the ECG electrodes 20 in the memory 17 (or the F-ROM 18) for each of the 12 leads. FIG. 4 is a graph schematically showing the electrocardiographic waveform data (vertical axis: electric potential (voltage), horizontal axis: time) recorded for one of the leads. As shown in FIG. 4, the CPU 10 extracts identified value (recognized value) data R (R potential or R-wave height), T (T potential or T-wave height), Q (Q potential or Q-wave height), ST (ST level), QT (QT interval), and RR (RR interval) based on the recognition of P-wave, Q-wave, R-wave, S-wave, ST-segment, and T-wave, respectively, in the electrocardiogram and records them in the memory 17 (or the F-ROM 18). The CPU 10 recognizes a heartbeat and each wave in the electrocardiogram by the following process, for example, when the waveform is normal.

(1) Recognition of a Heartbeat: After sampling electrocardiographic waveform data (potential or voltage value) for a predetermined period of time, the CPU 10 recognizes an R-wave, which is a local maximum component exceeding a prescribed threshold, and the next R-wave (a local maximum component exceeding a prescribed threshold) and recognizes the RR interval as a heartbeat. At this time, T-wave components, which are local maximums other than the R-waves (having a frequency lower than that of R-waves) may be removed with a low-cut filter.
(2) P-wave: A local maximum which appears 200 to 300 msec before an R-wave is recognized as a P-wave.
(3) Q-wave: A local minimum which appears immediately before an R-wave is recognized as a Q-wave.
(4) S-wave: A local minimum which appears immediately after an R-wave is recognized as an S-wave.
(5) T-wave: A local maximum which appears between two R-waves is recognized as a T-wave.
(6) ST-segment: A linear interpolation is performed between an S-wave and a T-wave on the electrocardiogram, and the part which appears as a local maximum component between them is recognized as an ST-segment.

In this embodiment, the trend of ST (ST level) (unit: mV, for example) is shown for each of the 12 leads in a graph.

Noises with abnormal periods may be generated and the extraction of identified value data cannot be made precisely depending on the motion of the patient during the measurement of electrocardiograms. As a method for removing such noises and obtaining precise identified value data, the technique disclosed in JP-A-Hei 6-261871, for example, may be used.

5. ST Level Trend Creation Process etc.

5-1. ST Level Trend Creation Process

Figure 6:
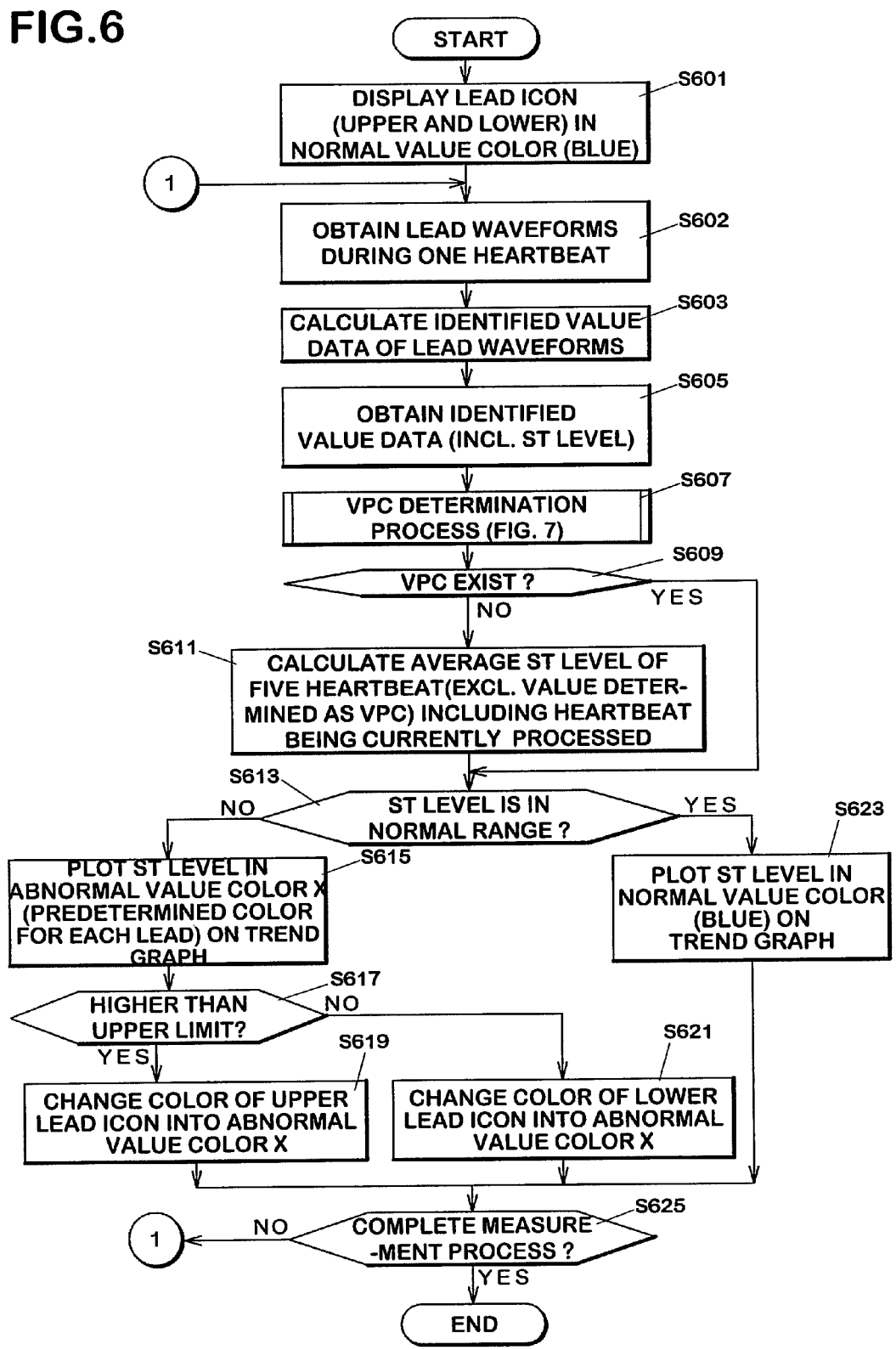
FIG. 6 is a flowchart of an ST level trend creation process.

Description will made of an ST level trend creation program of this embodiment with reference to the flowchart etc. in FIG. 6. The flowchart in FIG. 6 shows the content of an ST level trend creation program which is performed for one lead at a heartbeat. Thus, during the measurement of vital signs, the ST level trend creation process program shown in FIG. 6 is repeated at every heartbeat for all the 12 leads.

As a precondition of the ST level trend creation process, the CPU 10 of the ST level trend display device 100 displays lead icons in a normal value color (blue, for example) in the upper and lower part of the display screen 14 (step S601 in FIG. 6). The lead icons to be displayed are determined depending on the number of the ECG electrodes 20 for use in the measurement of electrocardiograms of the patient, that is, the subject leads. More specifically, when four ECG electrodes are used, six leads are displayed. Here, an example will be described in which 12-lead electrocardiograms are employed and 12 lead icons are displayed (see FIG. 5).

The CPU 10 measures 12-lead electrocardiograms via ECG electrodes 20 attached to the patient's body and an amplifier 11 and obtains lead waveforms (electrocardiographic waveforms) during one heartbeat (step S602).

The CPU 10 calculates identified value data of the lead waveforms (step S603 in FIG. 6) (refer FIG. 4 for the identified value data). The CPU 10 records the identified value data as the object of the ST level trend creation process in the F-ROM 18 or the memory 17 (step S605).

The identified value data as the object of the ST level trend creation process are the ST levels of five consecutive heartbeats including a heartbeat as the object to be displayed in the ST level trend graph and identified value data necessary for determination of a VPC, which will be described later.

FIG. 9 is a schematic view of identified value data as the object of the ST level trend creation process. The "No." is the number of heartbeat. For example, "−4" means the heartbeat which is four heartbeat before the present ("pre") heartbeat. In FIG. 9A, the ST level and so on designated as "Pre" are (current) identified value data to be obtained and calculated in step S602 and S603 in FIG. 6. At this time, the object of the ST level trend display is the ST level (designated as 202 in the drawing) of the heartbeat designated as No. "−2."

As described above, in this embodiment, the heartbeat on which the lead waveform obtaining process is performed and the heartbeat on which the ST level trend creation process is performed are different. The reason for it is, as described later, that the ST level of the heartbeat to be displayed is the average of the ST levels of five heartbeats including it. More specifically, the "identified value data as the object of the ST level trend creation process" which are recorded in step S605 include the ST levels of the "pre" to "−5" heartbeats (the data encircled by dotted line 200 in the drawing) and identified value data necessary for determination of a VPC in the heartbeat No. "−2." Description will be hereinafter made on the assumption that the object of the ST level trend display is the heartbeat No. "−2."

The CPU 10 performs a process for determining the presence or absence of a VPC (ventricular premature contraction) based on the identified value data (necessary for determination of a VPC in the heartbeat No. "−2") (step S607). The VPC determination process will be described later.

If it is determined that there is a VPC as a result of the VPC determination process, the CPU 10 performs the process in step S613 (on the ST level of the heartbeat No. "−2" (see the reference number 202 in FIG. 9)).

If it is determined that there is no VPC as a result of the VPC determination process in step S607, the CPU 10 calculates the average of the ST levels of five heartbeats including the heartbeat being currently processed (see the dotted line 200 in FIG. 9) and regards it as the ST level of the heartbeat being currently processed (step S611). When there is an ST level determined as indicating a VPC in the ST levels of the five heartbeats in step S609, the average of the ST levels is calculated excluding the value.

More specifically, when the display object is the ST level of the heartbeat No. "−2" (designated as 302) in FIG. 9B, and when the ST level of the heartbeat No. "−1" (designates as 304) has been determined as indicating "the presence of VPC", the value designated as 304 is excluded and the average of the four ST level values encircled by the dotted line 300 is calculated in step S611.

In this embodiment, determination of a VPC is exemplarily performed. One of the reasons for the VPC determination is to exclude (sudden) abnormal values which the ST levels may show when a VPC occurs from the calculation of average of the ST levels in the process in step S611 in FIG. 6. Thus, when a VPC occurred, only the ST level of the heartbeat is plotted on the graph.

After the process in step S609 or S611, the CPU 10 determines whether the ST level (or average of the ST levels) is in a normal range (step S613). In this embodiment, the normal range is −0.1 mV to 0.1 mV (upper limit: 0.1 mV, lower limit: −0.1 mV).

If it is determined that the ST level is in the normal range in the process in step S613, the CPU 10 draws (plots) the ST level on the trend graph in a normal value color (blue) (step S623).

If it is determined that the ST level is out of the normal range in the process in step S613, the CPU 10 draws the ST level on the trend graph in an abnormal value color X (step S615). Different colors are set as abnormal value colors (yellow, red, green, etc., for example) for each leads.

The CPU 10 then determines whether the ST level is higher than the upper limit (0.1 mV) (prescribed level) of the normal range (step S617). If it is determined that the ST level is higher than the upper limit, the CPU 10 changes the color of the lead icon in the upper part of the display screen 14 (the icon displayed in the upper part of the display screen of the lead icons for the lead from which the ST level is derived) to the abnormal value color X (step S619).

If it is determined that the ST level is not higher than the upper limit (that is, lower than the lower limit (prescribed level)) in step S617, the CPU 10 changes the color of the lead icon in the lower part of the display screen 14 (the icon displayed in the lower part of the display screen of the lead icons for the lead from which the ST level is derived) to the abnormal value color X (step S621).

When the ST level is higher than the upper limit, the trend curve of the ST level and the corresponding lead icon are displayed in the same manner as the curve 70 and the lead icon 60 shown in FIG. 5. When the ST level is lower than the lower limit, the trend curve of the ST level and the corresponding lead icon are displayed in the same manner as the curve 72 and the lead icon 62 shown in FIG. 5.

After the process in step S619, S621 or S623, the CPU 10 determines whether the measurement of the electrocardiogram has been completed (step S625). If not, the processes in and after step S602 are repeated. If it is determined that the measurement of the electrocardiogram has been completed, the CPU 10 finishes the ST level trend creation process.

The ST level trend creation process has been described. The program or algorithm for the process is illustrative and can be changed by means known to those skilled in the art. For example, in step S 617, it may be determined whether the value is lower than the lower limit or whether the value shows an upper abnormal value (when it is higher than the upper limit) or a lower abnormal value (when it is lower than the lower limit) instead of determining whether the ST level is higher than the upper limit (abnormality rank determination means).

The process of calculating the average of ST level values of five heartbeats in step S611 in FIG. 6 is illustrative. The average of the ST level values of a different number of heartbeats may be calculated. The process of calculating the average in step S611 and the VPC determination process in step S607 and S609 described later may be omitted.

5-2 VPC Determination Process

Figure 7:
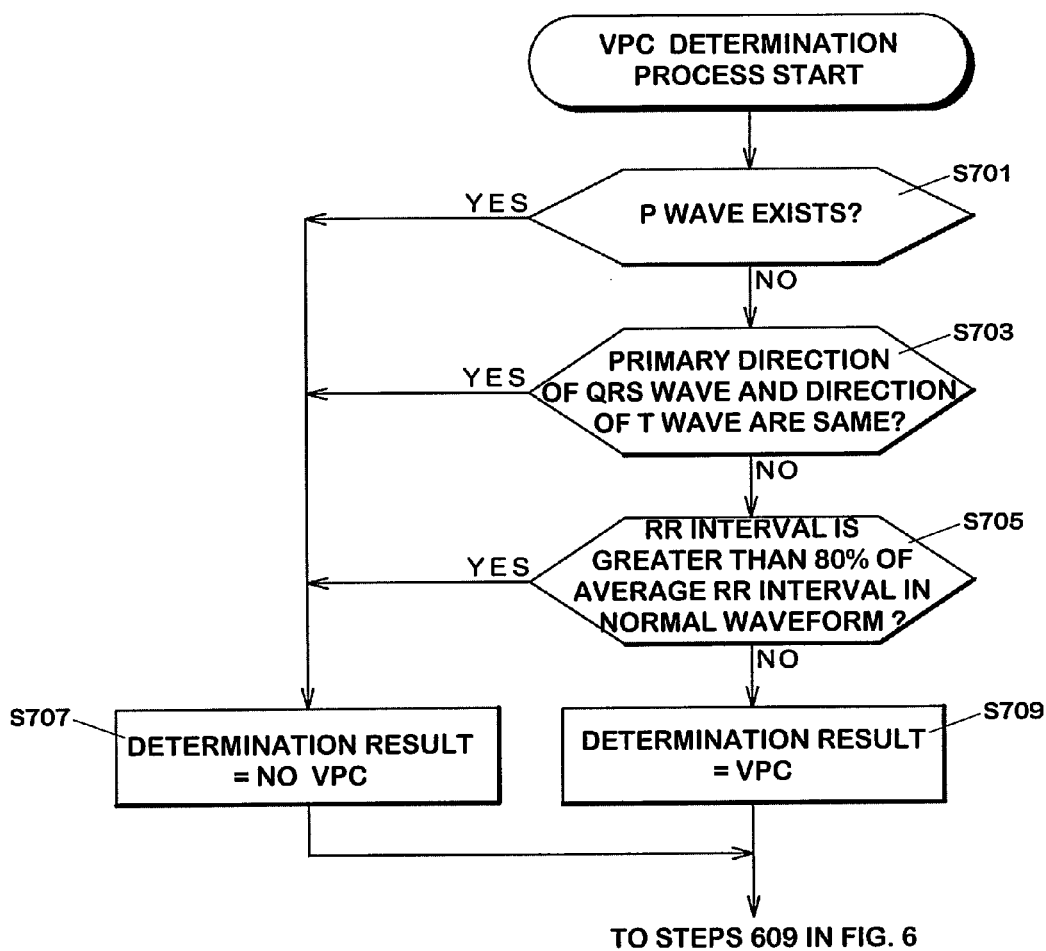
FIG. 7 is a flowchart of a VPC determination process.

FIG. 7 is a flowchart of an abnormality determination process for a ventricular premature contraction (VPC) which the CPU 10 performs in step S607 in FIG. 6. The determination of a VPC is to determine whether a ventricular premature contractions is occurring based on the ST level.

The CPU 10 of the ST level trend display device 100 determines whether there is a P-wave (step S701 in FIG. 7). If it is determined that there is a P-wave, the CPU 10 determines that "there is no VPC" (step S707). If it is determined that there is no P-wave, the CPU 10 determines whether the primary directions of QRS-waves are the same as the direction of T-waves (step S703).

If it is determined that the primary directions of QRS-waves are the same as the direction of T-waves, the CPU 10 performs the process in step S707. If it is determined that the primary directions of QRS-waves are not the same as the direction of T-waves, the CPU 10 determines whether the RR interval is greater than 80% of the average RR intervals in normal waveforms (step S705).

If it is determined that the RR interval is greater than 80% of the average RR intervals in normal waveforms, the CPU 10 performs the process in step S707. If it is determined that the RR interval is not greater than 80% of the average RR intervals in normal waveforms, the CPU 10 determines that "there is a VPC" (step S709).

Then, the CPU 10 performs the processes in and after step S609 in FIG. 6 based on the determination result obtained in the process in step S707 or step S709.

The VPC determination process has been described above. The determination process is illustrative and may be changed by means known to those skilled in the art. For example, a VPC may be determined by a method based on Minnesota Code criteria (or corrected criteria thereof). Also, something other than the ST level indicating a VPC (noises, for example) may be selected as the object to be excluded from the calculation of the average of ST levels in step S611.

6. Effects of Embodiment

According to the above embodiment, the user of the ST level trend display device 100 can check and determine the time-series trends of the ST levels obtained from lead waveforms derived from a plurality (12 at most) of leads (see FIG. 5).

In the embodiment, the lead icon 60 (for lead III) in the upper part of the display screen is displayed in the same abnormal value color X as the curve 70 to indicate that the ST level derived from the lead III (curve 70) is above the upper limit, for example, as shown in FIG. 5. Thus, there is a merit that the trend curves of ST levels obtained from a plurality of lead waveforms can be displayed simultaneously and that when some of the ST levels show abnormal values, the user can determine the names of the leads corresponding to the trend curves quickly and easily. In addition, the time at which the abnormal values appeared can be specified on the horizontal axis of the graph as shown in FIG. 5.

In the embodiment, the leads in which the ST level trend display device 100 is performing measurement are indicated by lead icons (see FIG. 5 and step S601 in FIG. 6). Thus, the user can visually determine the leads in which the ST level trend display device 100 is performing measurement (the information relating to the source of biological information).

In the embodiment, when an ST level shows an abnormal value, the corresponding lead icon is displayed in an abnormal value color, and, when the ST level returns to a normal value, the outer frame of the lead icon (the outer indication area) is maintained in the abnormal value color (while the inner area (inner indication area) of the lead icon is displayed in the normal value color) (see FIG. 5) (which corresponds to "the display means displays the information relating to the source of the biological information in such a manner that the case where the biological information is determined as abnormal biological information at the moment, the case where the biological information has not been determined as abnormal biological information, and the case where the biological information was determined as abnormal biological information in the past whereas it is not determined as abnormal biological information at the moment can be discriminated"). Thus, the user can visually recognize whether each of the ST levels derived from the leads has shown an abnormal value in the past with ease. The manner of displaying the history of abnormal values of the ST levels is not limited to this. The following variation can be used.

The variation of the manner of displaying the history of abnormal values of the ST levels is to change the color saturation of the information (lead icons) relating to the sources of the biological information depending upon whether the ST levels have shown abnormal values in the past. More specifically, the lead icons corresponding to the ST level trend curves which have shown abnormal values in the past (the values are normal at the moment) are displayed in an abnormal value color with low saturation (or a light color), and, when the ST levels show abnormal values, the lead icons are displayed in an abnormal value color with high saturation (or a dark color).

The method of displaying the history of abnormal values together with the trend of biological information can be expressed as follows.

"An indication area for indicating information relating to the source of the biological information, the indication area having an indication area for indicating the state of the biological information at the moment and an indication area for indicating the state of the biological information in the past, in which, when the biological information includes information determined as abnormal biological information in the past, the display means displays the indication area for indicating the state of the biological information in the past in association with the biological information determined as abnormal information."

In the embodiment, all the parts of the ST level trend curve within the normal range are displayed in the normal value color "a" (blue for example) (in the same trend display style) regardless of lead wave from which the ST levels are derived, as shown in FIG. 5. To display "in the same trend display style" includes to display the trends are displayed in the same style and to display them in such a manner that they can be determined as visually similar (or close) to each other. Thus, the display screen 14 can give a clear, not cluttered, impression to the user even when a plurality of ST level trend curves are displayed simultaneously on it. In addition, since the trend curves showing abnormal values and the corresponding lead icons are displayed in an abnormal value color on the display screen 14, the user can recognize the ST levels in abnormal conditions and the corresponding leads with ease.

7. Other Functions of the ST Level Trend Display Device

Functions other than the above-mentioned ST level trend generating process, of the ST level trend display device 100 will be described below.

7-1. Display of Heartbeat Condition

The ST level trend display device 100 displays a specific flashing symbol (or mark) in order to show a heartbeat condition (which corresponds to the term "means for outputting heartbeat-related information by varying display style"). More specifically, the CPU 10 processes a display of the flashing heart mark according to the heart rhythm measured, as illustrated in FIG. 5.

The user can confirm that the ST level trend display device 100 is running normally, and can also check the patient's heartbeat condition. In an alternative embodiment, the device outputs a specific sound (e.g. bleep sound) from the speaker 15 according to the heart rhythm, in conjunction with the flashing mark or instead of the flashing mark.

7-2. Warning for Impracticable Analysis

The ST level trend display device 100 displays a certain warning during the ST level trend generating process when an ECG electrode 20 etc. is detached from the patient or when trouble occurs in the generating process (which corresponds to the term "means for outputting warning signal when the biological information display process can not be executed"). More specifically, the CPU 10 displays a warning message stating "electrode detached" etc., on displaying area of "diagnostic information" on display 14.

The user who sees the warning can promptly understand that the ST level trend generating process has been interrupted by the trouble. In alternative embodiments, in order to draw the user's attention to the display, the CPU 10 changes the color of the whole display or the color of part of the display, or outputs a warning sound (e.g. an alarm sound).

8. Other Embodiments 8-1. Modification of Style of Displaying Trend of Biological Information Although an example of the style of displaying the trend graph of biological information is shown in FIG. 5 in the above embodiment, the present invention is not limited thereto. As another embodiment of the style of displaying the trend graph of biological information, display styles as shown in FIG. 8 may be employed. The outline of each display style will be described.

Figure 8A:
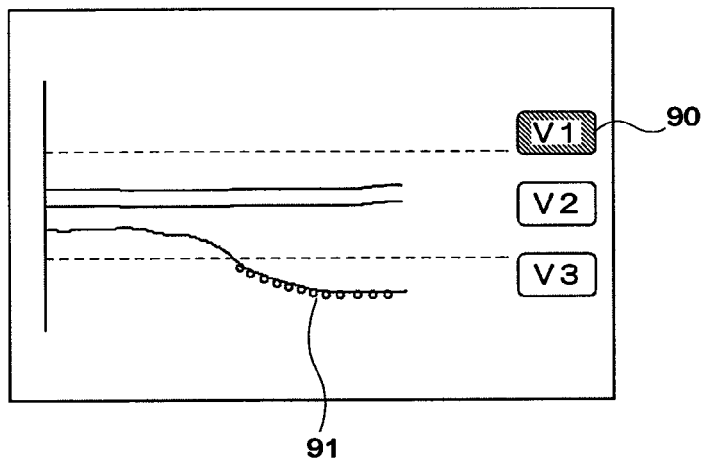
FIGS. 8A, 8B and 8C are modifications of the screen displayed on the ST trend level display device.

FIG. 8A shows an example in which the display position of the lead icons (source icons) is changed. In the drawing, the lead icons are displayed in a right part of the display screen. The color of the part of a curve 91 below the lower limit is changed to a color "a" and the color of a lead icon 90 is also changed to the color "a" to indicate that the source of the biological information for the curve 91 is the lead V1. The indicators showing the names of leads may be displayed in any part of the display screen.

Figure 8B:
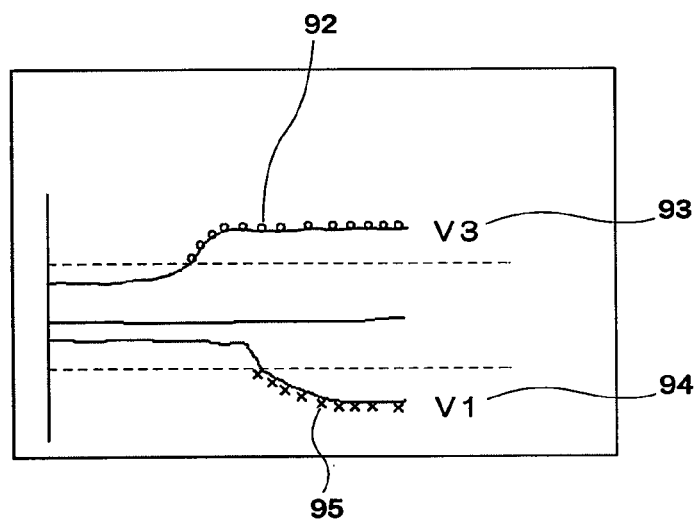

FIG. 8B shows an example in which, when biological information gets out of the normal range, the information showing the source of the biological information (information relating to the source, the name of lead) is shown in the vicinity of the corresponding trend curve. A curve 92 has a part above the upper limit of the normal range, and a lead indicator 93 (for the lead V3) is shown in the vicinity of the indicating point (plot point) of the curve. A curve 95 has a part below the lower limit of the normal range, and a lead indicator 94 (for the lead V1) is shown in the vicinity of the indicating point of the curve.

In the case shown in FIG. 8B, the information about the source is not shown when the biological information is in the normal range and shown only when the biological information shows an abnormal value. The trend curves of biological information within the normal range may not be shown depending on the setting by the user. Only when the biological information shows an abnormal value, the trend curve and the information about the source of the biological information are shown in association with each other. A trend curve of a representative value (or an average value) of a plurality of biological information may be displayed usually instead of displaying a plurality of biological information simultaneously. Individual curves of the biological information are shown only when the biological information shows an abnormal value.

Figure 8C:
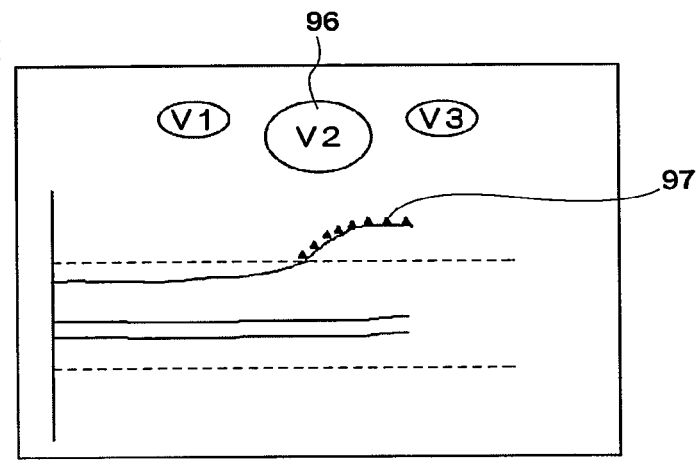

FIG. 8C shows a modification of the display style of lead icons (source icons). A curve 97 has exceeded the upper limit of the biological information, and the size of a lead icon 96 is changed to indicate that the source of the biological information shown as the curve 97 is the lead V2.

In the embodiments, displaying trend graph of ST level on display 14 is illustrated as an example of the "displaying means". In alternative embodiments of the "display means (or "output means"), the biological information can be outputted in computer-readable storage media such as memory card or CD-ROM. The biological information can be outputted to connection means (e.g. telephone lines, wireless communication, the Internet, wire communication, infrared data communication, mobile phone, Bluetooth, PHS, or the like). The biological information can be outputted as printed hard copy, facsimile, or the like.

The "biological trend displayed object" included in the claims is a concept that includes anything outputted so that the trend of biological information can be visually recognized. For example, a trend graph displayed on a display screen, outputted as a hard copy, outputted by a facsimile machine and so on are included in this concept.

8-2. Modification of Display Style of Abnormal Biological Information

The above embodiment is characterized in that when biological information shows an abnormal value, the information indicating the source of the biological information becomes easily recognizable to draw the attention of the user. As a method for associating abnormal biological information and the ground for it (source of the biological information) when a patient gets into an abnormal condition, the following variations may be employed.

A first variation for associating abnormal biological information and the source of it is to blink or flash the information (icon, for example) indicating the source of the biological information when the biological information shows an abnormal value.

A second variation is to perform a process for adding (or changing) a pattern (shape, symbol or code) indicating the source of the biological information when an abnormal value is detected. In this case, a process for adding (or changing) a pattern (type, shape, symbol or code) to the curve of the biological information may be performed to associate the source and the biological information obtained from the source. For example, the information indicating the source of the biological information showing an abnormal value (and/or the part of the graph of the biological information) may be displayed three-dimensionally so that it can look raised out.

Although blue is employed as a normal value color and red and yellow are employed as abnormal value colors in the above embodiment, other colors may be used. In general, however, it is advisable to use a discreet color with low saturation (low-saturation color or less recognizable color) for normal values and a outstanding color with high saturation (high-saturation color or highly recognizable color) for abnormal values. The color may be changed depending on the level of the abnormal value (the level of abnormality). More specifically, a color with low saturation is used when the difference from a normal value is small and a color with high saturation is used when the difference from the normal value is large.

Also, an alarm sound may be generated from speaker 15 as an aid to make the user recognize that biological information shows an abnormal value. In this case, the loudness or pitch of the sound may be changed depending on the source in which the abnormal value appears or the level of abnormality.

8-3. Modification of Biological Information

Although ST levels are shown as an example of biological information in the above embodiment, the present invention is not limited thereto. The present invention is applicable to biological information which is prescribed parameters acquired from a plurality of sources or measurement points and show different behaviors depending on the sources or the measurement points (which corresponds to "show different behaviors depending on the sources").

More specifically, in the case of an electrocardiogram, for example, R (R potential or R-wave height), T (T potential or T-wave height), Q (Q potential or Q-wave height), QT (QT interval) or RR (RR interval), which are values obtained by extracting the apex, start and end points of P-wave, Q-wave, R-wave, S-wave, ST segment, and T-wave, respectively, as components of a electrocardiographic waveform, may be employed as the "biological information."

More specifically, for example, trend curves of QT intervals in a plurality of leads are displayed and, when the QT intervals show abnormal values, the abnormal values and the name of the leads in which the abnormal values appeared are displayed in association with each other.

Alternatively, trend curves of identified values, such as ST level, QT interval, RR interval, in specific leads may be displayed as a plurality of pieces of "biological information." When the identified values show abnormal values, the trend curves having the abnormal values and the identified value names ("QT interval," for example) showing the abnormal values are displayed associated with each other.

The "data display device" according to the present invention can be implemented as a device for simultaneously monitoring the trends of a plurality of process values in a plant, for example, instead of biological information shown as an example in the above embodiment. In this case, when the process values are abnormal, the abnormal values are displayed on curves as "matters to be informed," and information indicating the devices in the plant (or parts of a device, component parts or the process values (parameters)) from which the process values were obtained are displayed in association with the curves. "To display in association with something" includes to display in a visually recognizable manner that the type of data and the curve of the data have a relation with each other, for example. For example, displaying the name of a parameter (type of data) and the curve of the data (a part of the curve display, the attribute of the curve display style or a component of the graph display style) in the same color is included.

8-4. Embodiments of Device Configuration

In the embodiments, the ST level trend display device 100 executes both ECG measurement and processes that generate and display ST level trend. In alternative embodiments, those functions can be separately executed by two or more discrete devices. For example, one device can execute an ECG measurement, outputting process for ST level (or identified value data), abnormality determining process for ST level, and outputting process for the determining result. The other device (which corresponds to "biological information trend display device") can execute inputting process for ST level and inputting process for the determining result of abnormality determination for ST level (which corresponds to "obtaining means"), and outputting process for ST level trend.

The configuration of the devices (the number and combination of devices) for performing the process of measuring electrocardiograms, the VPC determination process, the ST trend graph creation and display process, respectively, and the configuration of the CPU may be changed by means known to those skilled in the art.

Other auxiliary devices may be connected to the ST level trend display device 100. More specifically, a blood pressure meter may be connected to the ST level trend display device 100 as an auxiliary device to display "blood pressure (BP)" and a blood oxygen level meter to display "blood oxygen level ($SpO_2$)."

8-5. Application Embodiments of ST Level Trend Display Device

In the embodiments, the ST level trend display device 100 is used in ambulances. In alternative embodiments, the device can be used in any emergency medical arena in a portable form, used for home medical care by setting the device in a home, or used for living bodies including human or animals.

Devices that have similar functions with that of the ST level trend display device 100 can be installed in the driver's seat of an automobile or an electric train, an airplane cockpit, or the like, in order to prevent a serious accident from occurring when the driver develops a heart attack due to myocardial infarction etc. In other embodiments, such devices can be installed on a toilet seat, etc., for daily health care. For those applications, it is advantageous for the ECG electrodes 20 to be installed in an area with which the subject's body necessarily makes contact, such as a handle, toilet seat, handrail, or the like.

8-6. Program Execution

In the embodiments, the computer program for the CPU 10 is stored in the F-ROM 18. The computer program can be installed on the hard disk etc. from an installation CD-ROM (not shown). In alternative embodiments, the program can be installed from computer-readable storage media such DVD-ROM, a flexible disk (FD) or IC card (not shown). Alternatively, the program can be downloaded to the devices via the communications lines. The program storied on CD-ROM may also be directly executed although the program stored on CD-ROM can be executed indirectly by installing the program.

Computer-executable programs used in the embodiments include a program to be executable just after installation, a program that needs to be converted to another format (e.g. decompressing compressed data), or a program to be executable within a module.

A general description of the present invention as well as preferred embodiments of the invention has been set forth above. It is to be expressly understood, however, the terms described above are for purpose of illustration only and are not intended as definitions of the limits of the invention. Those skilled in the art to which the present invention pertains will recognize and be able to practice other variations in the system, device, and methods described which fall within the teachings of this invention. Accordingly, all such modifications are deemed to be within the scope of the invention.

What is claimed is:

1. A biological information trend display device for displaying a time series trend of biological information, comprising:
   an amplifier and analog-digital converter adapted to obtain a plurality of biological information;
   a CPU and a program stored in memory that determine whether the obtained biological information is abnormal biological information or not;
   a display and display controller that, based on the program, display a time-series trend for each of the plurality of biological information, wherein a color of the time-series trend determined as the abnormal biological information differs from the color of the time-series trend not determined as the abnormal biological information;
   wherein the program further instructs that a graph displaying area displays time-series trends for the plurality of biological information;
   wherein the program further instructs that a data type displaying area is provided for each source of the biological information of time-series trends;
   wherein the program further instructs that the time-series trends for the plurality of biological information are overlapped and displayed on the same graph displaying area;
   wherein the program further instructs that text showing the source of the biological information of time-series trends is displayed in the data type displaying area;
   wherein the program further instructs that a color of a background region of the data type displaying area for the source of the biological information determined as the abnormal biological information differs from the color of the background region of the data type displaying area for the source of the biological information not determined as the abnormal biological information;
   wherein the program further instructs that the color of the time-series trend determined as the abnormal biological information is the same as the color of the background region for the source of the biological information determined as the abnormal biological information;
   the CPU and the program stored in the memory are further adapted to:
      determine the obtained biological information as the abnormal biological information when the biological information exceeds a first level or falls below a second level;
      determine, based on whether the biological information exceeds a first level or falls below a second level, which text showing the source of abnormal biological information should be displayed;
      correlate the color of the time-series trend determined as the abnormal biological information with the same as the color of the background region for the source of the biological information determined as the abnormal biological information; and
   the display and display controller that, based on the program, display the text showing the source of abnormal biological information at an upper portion of the time-series trend when the biological information exceeds the first level, and display the text showing the source of abnormal biological information at a lower portion of the time-series trend when the biological information falls below the second level.

2. The device according to claim 1, wherein when subsequent biological information is no longer determined to be abnormal biological information, the display and the display controller display the trend of the subsequent biological information in the color for the normal biological information, and maintain the background region for the text showing the source of the biological information in the color for the abnormal biological information.

3. The device according to claim 1, wherein the background region allows differentiation between: a case in which current biological information is determined as the abnormal biological information, a case in which past and current biological information are not determined as the abnormal biological information, and a case in which past biological information is determined as the abnormal biological information while current biological information is not determined as the abnormal biological information.

4. The device according to claim 3, wherein the background region includes an inner indication area and an outer indication area that surrounds the inner indication area, and
wherein the display and the display controller display at least the inner indication area in the same color with the abnormal biological information when the current biological information is determined as the abnormal biological information, and display at least the outer indication area in the same color with the abnormal biological information when the biological information is determined as past abnormal biological information.

5. The device according to claim 1, wherein the display and the display controller display different time-series trends of the biological information in the same color, which are derived from different sources of the biological information that is not determined as the abnormal biological information.

6. The device according to claim 1, wherein the biological information comprises information related to an ST level of an electrocardiogram, and the text showing the source comprises information relating to an electrocardiogram lead.

7. A non-transitory computer readable media having stored thereon a computer program for a biological information trend display device that displays a time-series trend of biological information, wherein the computer program is implemented in a computer and capable of causing the computer to perform:
obtaining a plurality of biological information;
determining whether the obtained biological information is abnormal biological information or not;
displaying a time-series trend for each of the plurality of biological information, wherein a color of the time-series trend determined as the abnormal biological information differs from the color of the time-series trend not determined as the abnormal biological information;
wherein:
a graph displaying area is provided for time-series trends for the plurality of biological information;
a data type displaying area is provided for each source of the biological information of time-series trends;
the time-series trends for the plurality of biological information are overlapped and displayed on the same graph displaying area;
text showing the source of the biological information of time-series trends is displayed in the data type displaying area;
a color of a background region of the data type displaying area for the source of the biological information determined as the abnormal biological information differs from the color of the background region of the data type displaying area for the source of the biological information not determined as the abnormal biological information; and
the color of the time-series trend determined as the abnormal biological information is the same as the color of the background region for the source of the biological information determined as the abnormal biological information;
determining the obtained biological information as the abnormal biological information when the biological information exceeds a first level or falls below a second level;
determining, based on whether the biological information exceeds a first level or falls below a second level, which text showing the source of abnormal biological information should be displayed;
correlating the color of the time-series trend determined as the abnormal biological information with the same as the color of the background region for the source of the biological information determined as the abnormal biological information; and
displaying the text showing the source of abnormal biological information at an upper portion of the time-series trend when the biological information exceeds the first level, and displays the text showing the source of abnormal biological information at a lower portion of the time-series trend when the biological information falls below the second level.

8. A biological information trend display device for displaying a time-series trend of biological information, comprising:
an amplifier and analog-digital converter adapted to obtain a plurality of biological information and information regarding whether the biological information is abnormal biological information or normal biological information;
a display and display controller that, based on a program, display a time-series trend for each of the plurality of biological information, wherein a color of the time-series trend of the abnormal biological information differs from the color of the time-series trend of the normal biological information;
wherein the program further instructs that a graph displaying area is provided for time-series trends for the plurality of biological information;
wherein the program further instructs that a data type displaying area is provided for each source of the biological information of time-series trends;
wherein the program further instructs that the time-series trends for the plurality of biological information are overlapped and displayed on the same graph displaying area;
wherein the program further instructs that text showing the source of the biological information of time-series trend is displayed in the data type displaying area;
wherein the program further instructs that a color of a background region of the data type displaying area for the source of the biological information of the abnormal biological information differs from the color of the background region of the data type displaying region for the source of the biological information of the normal biological information;
wherein the program further instructs that the color of the time-series trend of the abnormal biological information is same as the color of the background region for the source of the biological information of the normal biological information;
a CPU and the program further:
determine the obtained biological information as the abnormal biological information when the biological information exceeds a first level or falls below a second level;

determine, based on whether the biological information exceeds a first level or falls below a second level, which text showing the source of abnormal biological information should be displayed;

correlate the color of the time-series trend determined as the abnormal biological information with the same as the color of the background region for the source of the biological information determined as the abnormal biological information; and the display and display controller that, based on the program, display the text showing the source of abnormal biological information at an upper portion of the time-series trend when the biological information exceeds the first level, and display the text showing the source of abnormal biological information at a lower portion of the time-series trend when the biological information falls below the second level.

9. A biological information trend display device for displaying a time-series trend of biological information, having a central processing unit (CPU), said central processing unit (CPU) of the biological information trend display device executing instructions that perform:

obtaining a plurality of biological information;

determining whether the obtained biological information is abnormal biological information or not; and displaying a time-series trend for each of the plurality of biological information, wherein a color of the time-series trend determined as the abnormal biological information differs from the color of the time-series trend not determined as the abnormal biological information;

wherein the instructions further provide a graph displaying area for time-series trends for the plurality of biological information;

wherein the instructions further provide a data type displaying area for each source of the biological information of the time-series trends;

wherein the instructions further provide that the time-series trends for the plurality of biological information are overlapped and displayed on the same graph displaying area;

wherein the instructions further instruct the display of text showing the source of the biological information of time-series trends in the data type displaying area;

wherein the instructions further provide that a color of a background region of the data type displaying area for the source of the biological information determined as the abnormal biological information differs from the color of the background region of the data type displaying area for the source of the biological information not determined as the abnormal biological information;

wherein the instructions further provide the color of the time-series trend determined as the abnormal biological information is the same as the color of the background region for the source of the biological information determined as the abnormal biological information;

the CPU and the instructions further:

determine the obtained biological information as the abnormal biological information when the biological information exceeds a first level or falls below a second level;

determine, based on whether the biological information exceeds a first level or falls below a second level, which text showing the source of abnormal biological information should be displayed;

correlate the color of the time-series trend determined as the abnormal biological information with the same as the color of the background region for the source of the biological information determined as the abnormal biological information; and the CPU and a display controller, based on the instructions, further display the text showing the source of abnormal biological information at an upper portion of the time-series trend when the biological information exceeds the first level, and display the text showing the source of abnormal biological information at a lower portion of the time-series trend when the biological information falls below the second level.

10. A biological information trend display device for displaying a time-series trend of biological information, having a central processing unit (CPU), said central processing unit (CPU) of the biological information trend display device executing instructions that perform:

obtaining a plurality of biological information and information regarding whether the biological information is abnormal biological information or normal biological information; and displaying a time-series trend for each of the plurality of biological information, wherein a color of the time-series trend of the abnormal biological information differs from the color of the time-series trend of the normal biological information;

wherein the instructions further provide a graph displaying area for time-series trends for the plurality of biological information;

wherein the instructions further provide a data type displaying area for each source of the biological information of time-series trends;

wherein the instructions further provide that the time-series trends for the plurality of biological information are overlapped and displayed on the same graph displaying area;

wherein the instructions further instruct the display of text showing the source of the biological information of time-series trends in the data type displaying area;

wherein the instructions further provide that a color of a background region of the data type displaying area for the source of the biological information of the abnormal biological information differs from the color of the background region of the data type displaying region for the source of the biological information of the normal biological information;

wherein the instructions further provide the color of the time-series trend of the abnormal biological information is same as the color of the background region for the source of the biological information of the abnormal biological information;

the CPU and the instructions further:

determine the obtained biological information as the abnormal biological information when the biological information exceeds a first level or falls below a second level;

determine, based on whether the biological information exceeds a first level or falls below a second level, which text showing the source of abnormal biological information should be displayed;

correlate the color of the time-series trend determined as the abnormal biological information with the same as the color of the background region for the source of the biological information determined as the abnormal biological information; and a display and display controller that, based on the instructions, display the text showing the source of abnormal biological information at an upper portion of the time-series trend when the biological information exceeds the first level, and display the text showing the source of abnormal biological information at a lower portion of the time-series trend when the biological information falls below the second level.

11. A method for displaying a time-series trend of a biological information trend, comprising:
   obtaining a plurality of biological information;
   determining, by a processor, whether the obtained biological information is abnormal biological information or not;
   displaying a time-series trend for each of the plurality of biological information, wherein a color of the time-series trend determined as the abnormal biological information differs from the color of the time-series trend not determined as the abnormal biological information;
   wherein:
      a graph displaying area is provided for time-series trends for the plurality of biological information;
      a data type displaying area is provided for each source of the biological information of time-series trends;
      the time-series trends for the plurality of biological information are overlapped and displayed on the same graph displaying area;
      text showing the source of the biological information of time-series trends is displayed in the data type displaying area;
      a color of a background region of the data type displaying area for the source of the biological information determined as the abnormal biological information differs from the color of the background region of the data type displaying area for the source of the biological information not determined as the abnormal biological information;
      a color of the time-series trend determined as the abnormal biological information is same as the color of the background region for the source of the biological information determined as the abnormal biological information;
   determining the obtained biological information as the abnormal biological information when the biological information exceeds a first level or falls below a second level;
   determining, based on whether the biological information exceeds a first level or falls below a second level, which text showing the source of abnormal biological information should be displayed;
   correlating the color of the time-series trend determined as the abnormal biological information with the same as the color of the background region for the source of the biological information determined as the abnormal biological information; and
   displaying the text showing the source of abnormal biological information at an upper portion of the time-series trend when the biological information exceeds the first level, and displays the text showing the source of abnormal biological information at a lower portion of the time-series trend when the biological information falls below the second level.

12. A biological information trend display device for displaying a time series trend of biological information, comprising:
   an amplifier and analog-digital converter adapted to obtain a plurality of biological information;
   a CPU and a program stored in a memory that determine whether he obtained biological information is abnormal biological information or not;
   a display and display controller that, based on the program, display a time-series trend for each of the plurality of biological information, wherein a color of the time-series trend determined as the abnormal biological information differs from the color of the time-series trend not determined as the abnormal biological information;
   wherein the program further instructs that a graph displaying area is provided for time-series trends for the plurality of biological information;
   wherein the program further instructs that a data type displaying area is provided for each source of the biological information of time-series trends;
   wherein the program further instructs that the time-series trends for the plurality of biological information are overlapped and displayed on the same graph displaying area;
   wherein the program further instructs that text showing the source of the biological information of time-series trends is displayed in the data type displaying area;
   wherein the program further instructs that a color of the text of the data type displaying area for the source of the biological information determined as the abnormal biological information differs from the color of the text of the data type displaying region for the source of the biological information not determined as the abnormal biological information;
   wherein the program further instructs that the color of the time-series trend determined as the abnormal biological information is the same as the color of the text for the source of the biological information determined as the abnormal biological information;
   the CPU and the program stored in the memory are further adapted to:
      determine the obtained biological information as the abnormal biological information when the biological information exceeds a first level or falls below a second level;
      determine, based on whether the biological information exceeds a first level or falls below a second level, which text showing the source of abnormal biological information should be displayed;
      correlate the color of the time-series trend determined as the abnormal biological information with the same as the color of the background region for the source of the biological information determined as the abnormal biological information; and
   the display and the display controller that, based on the program, display the text showing the source of abnormal biological information at an upper portion of the time-series trend when the biological information exceeds the first level, and display the text showing the source of abnormal biological information at a lower portion of the time-series trend when the biological information falls below the second level.

13. The device according to claim 12, wherein when subsequent biological information is no longer determined to be abnormal biological information, the display and the display controller display the trend of the subsequent biological information in the color for the normal biological information, and maintains the text for showing the source of the biological information in the color for the abnormal biological information.

14. The device according to claim 12, wherein the data type displaying area includes a background region for each text showing the source of the biological information and the background region allows differentiation between: a case in which current biological information is determined as the abnormal biological information, a case in which past and current biological information are not determined as the abnormal biological information, and a case in which past biological information is determined as the abnormal biological information while current biological information is not determined as the abnormal biological information.

15. The device according to claim 14, wherein the background region includes an inner indication area and an outer indication area that surrounds the inner indication area, and
wherein the display and the display controller display at least the inner indication area in the same color with the abnormal biological information when current biological information is determined as the abnormal biological information, and displays at least the outer indication area in the same color with the abnormal biological information when the biological information is determined as past abnormal biological information.

16. The device according to claim 12, wherein the display and the display controller display different time-series trends of the biological information in the same color, which are derived from different sources of the biological information that is not determined as the abnormal biological information.

17. The device according to claim 12, wherein the biological information comprises information related to an ST level of an electrocardiogram, and the text showing the source comprises information relating to an electrocardiogram lead.

18. A non-transitory computer readable media having stored thereon a computer program for a biological information trend display device that displays a time-series trend of biological information, wherein the computer program is implemented in a computer and capable of causing the computer to perform:
obtaining a plurality of biological information;
determining whether the obtained biological information is abnormal biological information or not;
displaying a time-series trend for each of the plurality of biological information, wherein a color of the time-series trend determined as the abnormal biological information differs from the color of the time-series trend not determined as the abnormal biological information;
wherein:
a graph displaying area is provided for time-series trends for the plurality of biological information;
a data type displaying area is provided for each source of the biological information of time-series trends;
the time-series trends for the plurality of biological information are overlapped and displayed on the same graph displaying area;
text showing the source of the biological information of time-series trends is displayed in the data type displaying area;
a color of the text of the data type displaying area for the source of the biological information determined as the abnormal biological information differs from the color of the text of the data type displaying area for the source of the biological information not determined as the abnormal biological information;
the color of the time-series trend determined as the abnormal biological information is the same as the color of the text for the source of the biological information determined as the abnormal biological information;
determining the obtained biological information as the abnormal biological information when the biological information exceeds a first level or falls below a second level;
determining, based on whether the biological information exceeds a first level or falls below a second level, which text showing the source of abnormal biological information should be displayed;
correlating the color of the time-series trend determined as the abnormal biological information with the same as the color of the background region for the source of the biological information determined as the abnormal biological information; and
displaying the text showing the source of abnormal biological information at an upper portion of the time-series trend when the biological information exceeds the first level, and displays the text showing the source of abnormal biological information at a lower portion of the time-series trend when the biological information falls below the second level.

19. A biological information trend display device for displaying a time-series trend of biological information, comprising:
an amplifier and analog-digital converter adapted to obtain a plurality of biological information and information regarding whether the biological information is abnormal biological information or normal biological information; and
a display and display controller that, based on a program, display a time-series trend for each of the plurality of biological information, wherein a color of the time-series trend of the abnormal biological information differs from the color of the time-series trend of the normal biological information;
wherein the program further instructs that a graph displaying area is provided for time-series trends for the plurality of biological information;
wherein the program further instructs that a data type displaying area is provided for each source of the biological information of time-series trends;
wherein the program further instructs that the time-series trends for the plurality of biological information are overlapped and displayed on the same graph displaying area;
wherein the program further instructs that text showing the source of the biological information of time-series trends is displayed in the data type displaying area;
wherein the program further instructs that a color of the text of the data type displaying area for the source of the biological information of the abnormal biological information differs from the color of the text of the data type displaying area for the source of the biological information of the normal biological information;
wherein the program further instructs that the color of the time-series trend of the abnormal biological information is the same as the color of the text for the source of the biological information of the abnormal biological information;
a CPU and the program further:
determine the obtained biological information as the abnormal biological information when the biological information exceeds a first level or falls below a second level;
determine, based on whether the biological information exceeds a first level or falls below a second level, which text showing the source of abnormal biological information should be displayed;

correlate the color of the time-series trend determined as the abnormal biological information with the same as the color of the background region for the source of the biological information determined as the abnormal biological information; and the display and display controller that, based on the program, display the text showing the source of abnormal biological information at an upper portion of the time-series trend when the biological information exceeds the first level, and display the text showing the source of abnormal biological information at a lower portion of the time-series trend when the biological information falls below the second level.

20. A biological information trend display device for displaying a time-series trend of biological information, having a central processing unit (CPU), said central processing unit (CPU) of the biological information trend display device executing instructions that perform:

obtaining a plurality of biological information;

determining whether the obtained biological information is abnormal biological information or not; and displaying a time-series trend for each of the plurality of biological information, wherein a color of the time-series trend determined as the abnormal biological information differs from the color of the time-series trend not determined as the abnormal biological information;

wherein the instructions further provide a graph displaying area for time-series trends for the plurality of biological information;

wherein the instructions further provide a data type displaying area for each source of the biological information of time-series trends;

wherein the instructions further provide the time-series trends for the plurality of biological information are overlapped and displayed on the same graph displaying area;

wherein the instructions further instruct the display of text showing the source of the biological information of time-series trends in the data type displaying area;

wherein the instructions further provide a color of the text of the data type displaying area for the source of the biological information determined as the abnormal biological information differs from the color of the text of the data type displaying area for the source of the biological information not determined as the abnormal biological information;

wherein the instructions further provide the color of the time-series trend determined as the abnormal biological information is the same as the color of the text for the source of the biological information determined as the abnormal biological information;

the CPU and the instructions further:

determine the obtained biological information as the abnormal biological information when the biological information exceeds a first level or falls below a second level;

determine, based on whether the biological information exceeds a first level or falls below a second level, which text showing the source of abnormal biological information should be displayed;

correlate the color of the time-series trend determined as the abnormal biological information with the same as the color of the background region for the source of the biological information determined as the abnormal biological information; and the CPU and a display controller, based on the instructions, further display the text showing the source of abnormal biological information at an upper portion of the time-series trend when the biological information exceeds the first level, and display the text showing the source of abnormal biological information at a lower portion of the time-series trend when the biological information falls below the second level.

21. A biological information trend display device for displaying a time-series trend of biological information, having a central processing unit (CPU), said central processing unit (CPU) of the biological information trend display device executing instructions that perform:

obtaining a plurality of biological information and information regarding whether the biological information is abnormal biological information or normal biological information; and displaying a time-series trend for each of the plurality of biological information, wherein a color of the time-series trend of the abnormal biological information differs from the color of the time-series trend of the normal biological information;

wherein the instructions further provide a graph displaying area is provided for time-series trends for the plurality of biological information;

wherein the instructions further provide a data type displaying area is provided for each source of the biological information of time-series trends;

wherein the instructions further provide the time-series trends for the plurality of biological information are overlapped and displayed on the same graph displaying area;

wherein the instructions further instruct the display of text showing the source of the biological information of time-series trends is displayed in the data type displaying area;

wherein the instructions further provide a color of the text of the data type displaying area for the source of the biological information of the abnormal biological information differs from the color of the text of the data type displaying region for the source of the biological information of the normal biological information;

wherein the instructions further provide that the color of the time-series trend of the abnormal biological information is the same as the color of the text for the source of the biological information of the abnormal biological information;

the CPU and the instructions further:

determine the obtained biological information as the abnormal biological information when the biological information exceeds a first level or falls below a second level;

determine, based on whether the biological information exceeds a first level or falls below a second level, which text showing the source of abnormal biological information should be displayed;

correlate the color of the time-series trend determined as the abnormal biological information with the same as the color of the background region for the source of the biological information determined as the abnormal biological information; and the CPU and a display controller, based on the instructions, further display the text showing the source of abnormal biological information at an upper portion of the time-series trend when the biological information exceeds the first level, and display the text showing the source of abnormal biological information at a lower portion of the time-series trend when the biological information falls below the second level.

22. A method for displaying a time-series trend of a biological information trend, comprising:
   obtaining a plurality of biological information;
   determining, by a processor, whether the obtained biological information is abnormal biological information or not;
   displaying a time-series trend for each of the plurality of biological information, wherein a color of the time-series trend determined as the abnormal biological information differs from the color of the time-series trend not determined as the abnormal biological information;
   wherein:
      a graph displaying area is provided for time-series trends for the plurality of biological information;
      a data type displaying area is provided for each source of the biological information of time-series trends;
      the time-series trends for the plurality of biological information are overlapped and displayed on the same graph displaying area;
      text showing the source of the biological information of time-series trends is displayed in the data type displaying area;
      a color of the text of the data type displaying area for the source of the biological information determined as the abnormal biological information differs from the color of the text of the data type displaying region for the source of the biological information not determined as the abnormal biological information;
      the color of the time-series trend determined as the abnormal biological information is the same as the color of the text for the source of the biological information determined as the abnormal biological information;
   determining the obtained biological information as the abnormal biological information when the biological information exceeds a first level or falls below a second level;
   determining, based on whether the biological information exceeds a first level or falls below a second level, which text showing the source of abnormal biological information should be displayed;
   correlating the color of the time-series trend determined as the abnormal biological information with the same as the color of the background region for the source of the biological information determined as the abnormal biological information; and
   displaying the text showing the source of abnormal biological information at an upper portion of the time-series trend when the biological information exceeds the first level, and displays the text showing the source of abnormal biological information at a lower portion of the time-series trend when the biological information falls below the second level.

* * * * *